(12) United States Patent
Lee

(10) Patent No.: US 8,143,373 B2
(45) Date of Patent: Mar. 27, 2012

(54) CARBOHYDRATE-CONTAINING PAN CANCER MARKER

(75) Inventor: Chi-Yu Gregory Lee, Vancouver (CA)

(73) Assignee: Vancouver Biotech Ltd., Vancouver (CA)

( * ) Notice: Subject to any disclaimer, the term of this patent is extended or adjusted under 35 U.S.C. 154(b) by 0 days.

(21) Appl. No.: 12/599,284

(22) PCT Filed: May 14, 2008

(86) PCT No.: PCT/CA2008/000932
§ 371 (c)(1),
(2), (4) Date: Oct. 19, 2010

(87) PCT Pub. No.: WO2008/138139
PCT Pub. Date: Nov. 20, 2008

(65) Prior Publication Data
US 2011/0033445 A1    Feb. 10, 2011

Related U.S. Application Data

(60) Provisional application No. 60/917,906, filed on May 14, 2007, provisional application No. 61/044,028, filed on Apr. 10, 2008.

(51) Int. Cl.
*C07K 4/00* (2006.01)
(52) U.S. Cl. .................................................. 530/300
(58) Field of Classification Search .................. 530/300
See application file for complete search history.

(56) References Cited

U.S. PATENT DOCUMENTS 5,530,101 A * 6/1996 Queen et al.
5,650,291 A * 7/1997 Lee ............................ 435/344.1
2002/0155121 A1* 10/2002 Devico et al. ............. 424/186.1

FOREIGN PATENT DOCUMENTS
WO     WO 2005037261 A1 *   4/2005

OTHER PUBLICATIONS

Fundamental Immunology, William E. Paul, M.D. ed., 3rd ed., p. 242, 1993.*
International Search Report for PCT/CA2008/000932, mailed on Aug. 1, 2008, 2 pages.
International Preliminary Report on Patentability for PCT/CA2008/000932, completed on Aug. 12, 2009, 8 pages.
Lee et al., Cancer Immunol. Immunother. (1992) 35:19-26.
Lee et al., J. Clin. Ligand Assay (2006) 29:47-51.
Lee et al., Journal of Gynecology and Obstetrics (1995) 49(Supp.):S27-S32.
Lee et al., Cancer Immunology and Immunotherapy (1992) 35(1):19-26.
Lee et al., Proceedings of the American Association for Cancer Research Annual Meeting (2008) 49:1059-1060.
Supplemental European Search Report for EP 08757092.5, mailed Mar. 14, 2011, 12 pages.

* cited by examiner

*Primary Examiner* — Misook Yu
*Assistant Examiner* — Brad Duffy
(74) *Attorney, Agent, or Firm* — Morrison & Foerster LLP

(57) ABSTRACT

The effective epitope of CA215, a known cancer marker and antigen, has been demonstrated to include a carbohydrate moiety of defined composition and to be non-reactive with anti-human IgG, IgA and IgM, although CA215 is an immunoglobulin heavy chain-like molecule. The defined epitope may be used to prepare immunogenic compositions for treatment and prevention of cancers in humans and may be optimized as to protocol and formulation in animal model systems. Improved protocols for diagnosis and treatment are also described.

3 Claims, 7 Drawing Sheets

Full ESI-MS of released N-linked glycans from human IgG

Full ESI-MS of released N-linked glycans from RP 215 Mab

Full ESI-MS of released N-linked glycans from CA 215 sample

Full ESI-MS of released N-linked glycans from CA 215 sample

Full ESI-MS of released N-linked glycans from CA 215 sample

CARBOHYDRATE-CONTAINING PAN CANCER MARKER

CROSS-REFERENCE TO RELATED APPLICATIONS

This application is the national phase of PCT application PCT/CA2008/000932 having an international filing date of 14 May 2008, which claims priority to U.S. Provisional Application Ser. No. 60/917,906 filed 14 May 2007 and U.S. Provisional Application Ser. No. 61/044,028 filed 10 Apr. 2008. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 616342000100Seqlist.txt | Sep. 24, 2010 | 52,993 bytes |

TECHNICAL FIELD

The invention relates to the field of protein markers that can distinguish cancer cells or tissues from normal cells or tissues and are found on many tumors in human subjects. More specifically, the invention relates to the carbohydrate-containing epitope of the known cancer marker CA215 and to methods of using this epitope.

BACKGROUND ART

U.S. Pat. No. 5,650,291 ('291) incorporated herein by reference describes the isolation of a tumor-associated antigen, CA215, which is present on an ovarian tumor cell line, and is also displayed on many tumors in humans. Monoclonal antibodies were prepared to this antigen, including the monoclonal antibody RP215. The hybridoma cell line that produces this antibody was deposited at the American Type Culture Collection under the terms of the Budapest Treaty on 5 Apr. 1989 as ATCC HB10095. The current address of ATCC is P.O. Box 1549, Manassas, Va. 20108. The '291 patent describes CA215 as having a minimum molecular weight of 60 kD on SDS gels when identified with RP215. However, aggregates with molecular weights ranging from 100 kD to 2,000 kD were also shown to be present. CA215 was purified by immunoaffinity chromatographic procedures and could be purified either from an extract of cultured ovarian tumor cells (OC-3-VGH) or from the shed culture medium of these cells. The CA215 antigen is characterized as a "membrane associated" soluble antigen which can be detected by RP215 in sera of patients with ovarian or cervical cancer. The antigen could not be detected in any normal tissue. This antigen and the monoclonal antibody that recognizes it were also described in an article by Lee, C. Y. G., et al., *Cancer Immunol. Immunother.* (1992) 35:19-26. CA215 was denominated Cox-1 in that article In a later paper, authored by the same group, Lee, G., et al., *J. Clin. Ligand Assay* (2006) 29:47-51, it was reported that treatment with periodate at neutral pH virtually eliminated the immunoreactivity of CA215 in a sandwich assay employing RP215. This led the authors to the conclusion that the epitope of CA215 reactive with RP215 may comprise carbohydrate.

It appears that the epitope of CA215 recognized by RP215 is present on approximately 60% of all cancers. Further information on its distribution is found in Lee, G., et al., *J. Clin. Ligand Assay* (2006) supra.

The '291 patent further describes a method to determine the location of tumors bearing the antigen CA215 by utilizing the antibodies immunoreactive against it to label cells that produce this antigen. Labeling the monoclonal antibodies with various radioisotopes was described as well as conjugating toxins to these antibodies and administration of the antibodies or immunotoxins for therapeutic use.

The present invention further refines the work described in these publications by demonstrating that the carbohydrate portion of the epitope is located at the variable region of immunoglobulin heavy chain-like molecules, thus making possible compositions which comprise only the relevant portions of CA215 for inclusion in vaccines or for generating and purifying antibodies useful in imaging of targeted cancer cells. This work also demonstrates that there are two forms of CA215—one membrane-bound and another that is secreted.

DISCLOSURE OF THE INVENTION

The invention is directed to compositions that consist essentially of the epitope region of CA215. This epitope region comprises a carbohydrate and optionally at least a portion of an immunoglobulin heavy-chain like variable region amino acid sequence. This epitope is specifically immunoreactive with RP215 monoclonal antibody, but is not significantly immunoreactive with anti-human IgG.

In other aspects, the invention relates to the use of the minimal epitope or antiidiotype antibodies that mimic it as active ingredients in therapeutic and prophylactic methods to treat cancer. The epitope and antiidiotype antibodies can also be used as reagents for affinity purification of and for identification of additional monoclonal antibodies useful as diagnostic or therapeutic reagents for cancers.

In another aspect, the invention relates to improvements in immunoassays for CA215 using an alternative monoclonal antibody directed against this antigen or an antibody that is immunoreactive with IgG as a component in a new sandwich assay.

In other aspects, the invention relates to improved monoclonal antibodies which are modified forms of RP215, including humanized forms. Humanized forms of RP215 are useful in therapeutic methods, and can be conjugated to additional antineoplastic moieties to improve targeting of such moieties.

In additional aspects, the invention relates to protocols that take advantage of the dual secreted/membrane-bound nature of the CA215 antigen. In such protocols, diagnosis in body fluids by detection of the secreted form is effected, optionally using the improved assay system of the present invention followed by localization and treatment of solid tumors using the invention antibodies in humanized form optionally coupled to cytotoxic agents for treatment or radioisotopes for localization and/or treatment.

MODES OF CARRYING OUT THE INVENTION

Figure 1:
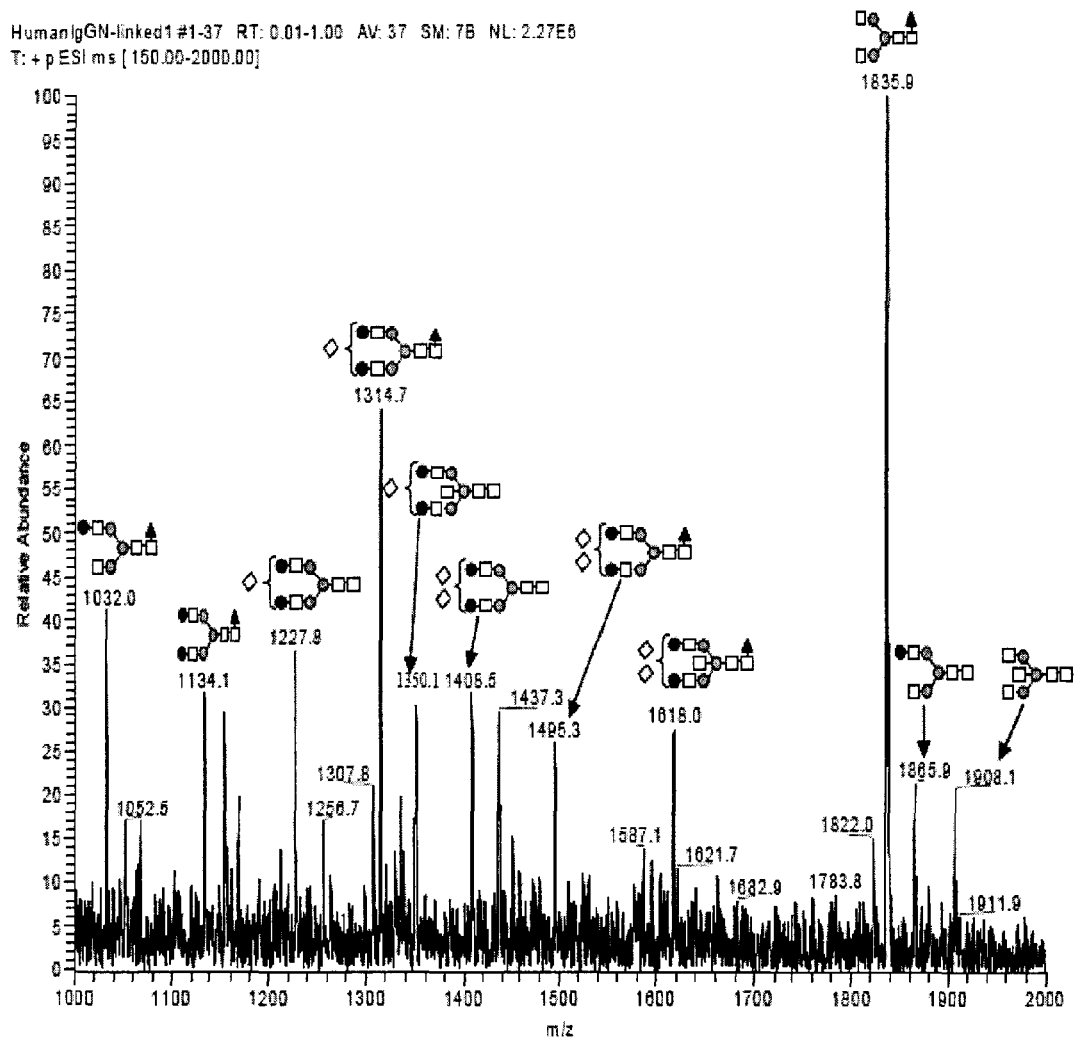
FIGS. 1-5 are full ESI-MS spectra of released N-linked glycans from human IgG, RP215 mAb, and three samples of CA215 respectively.
Figure 2:
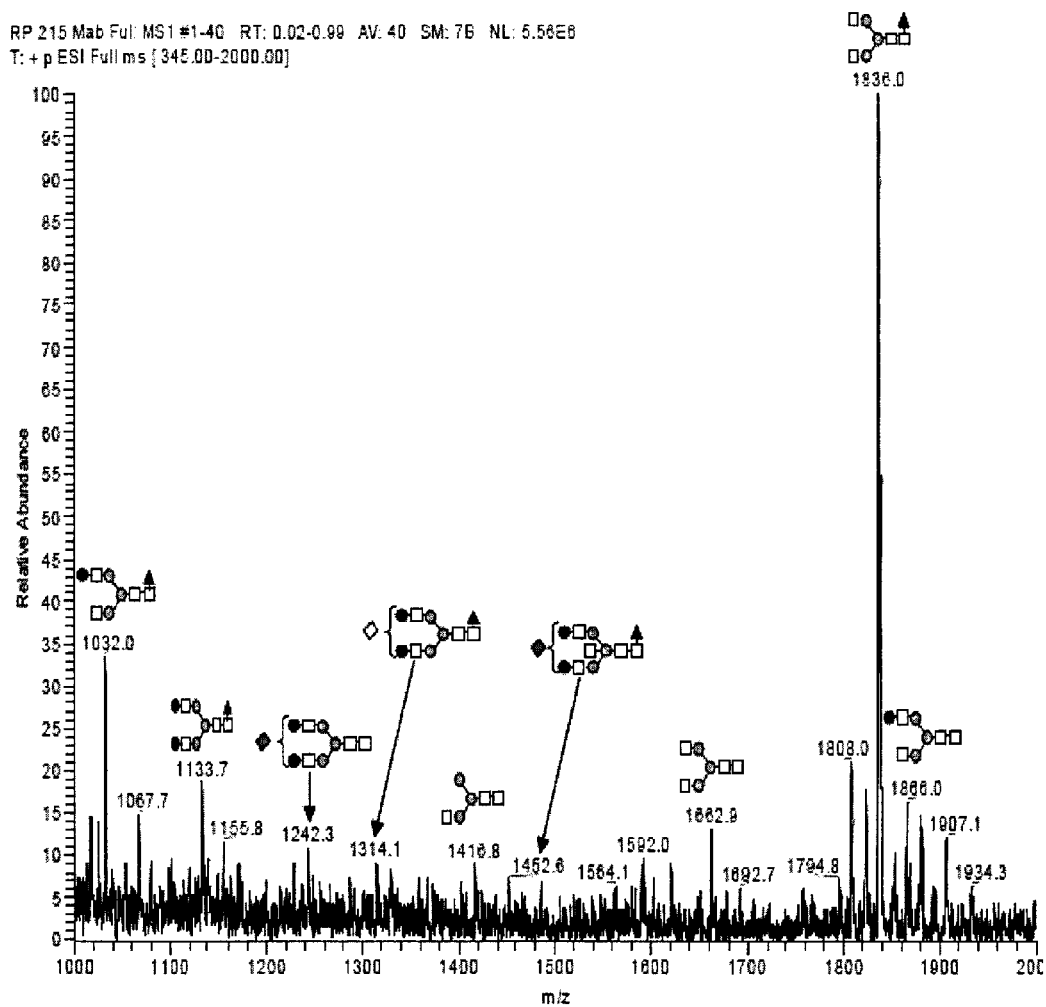
Figure 3:
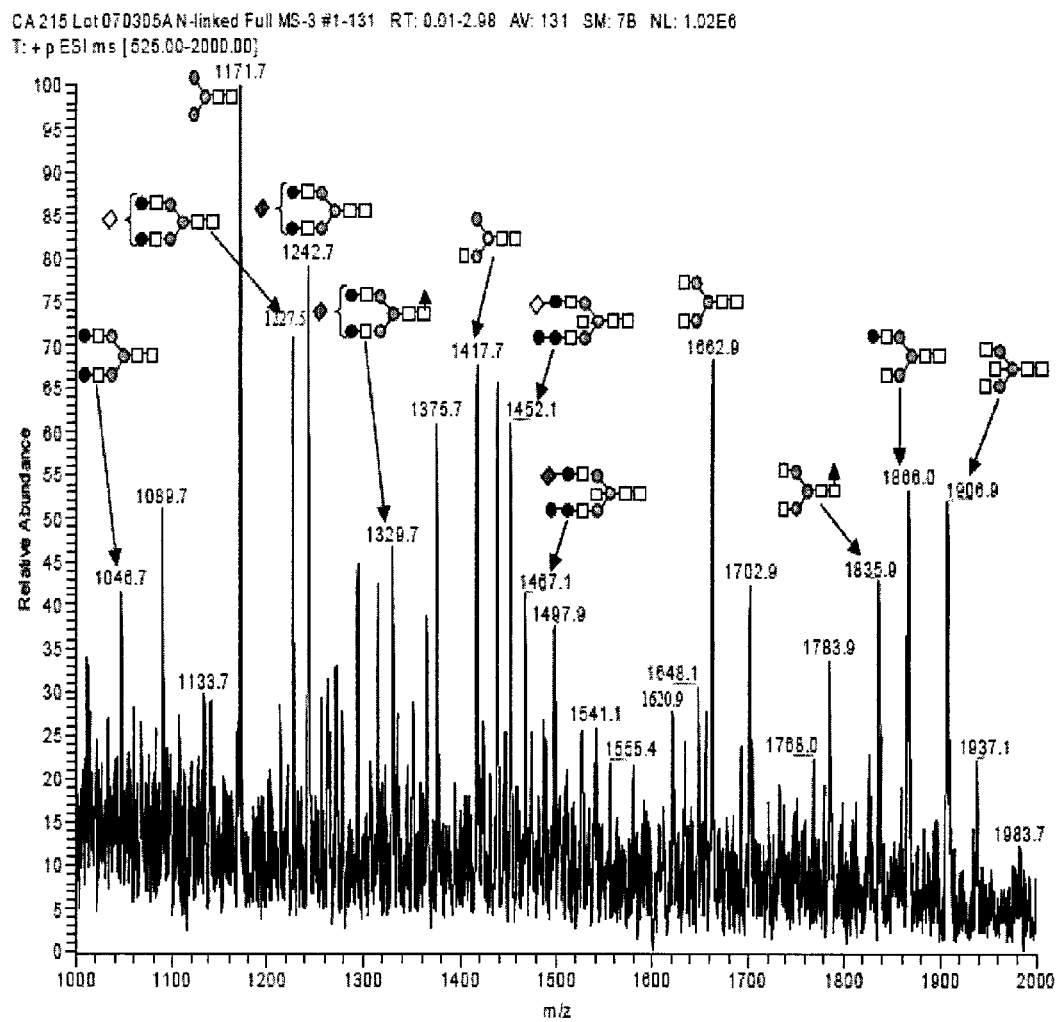
Figure 4:
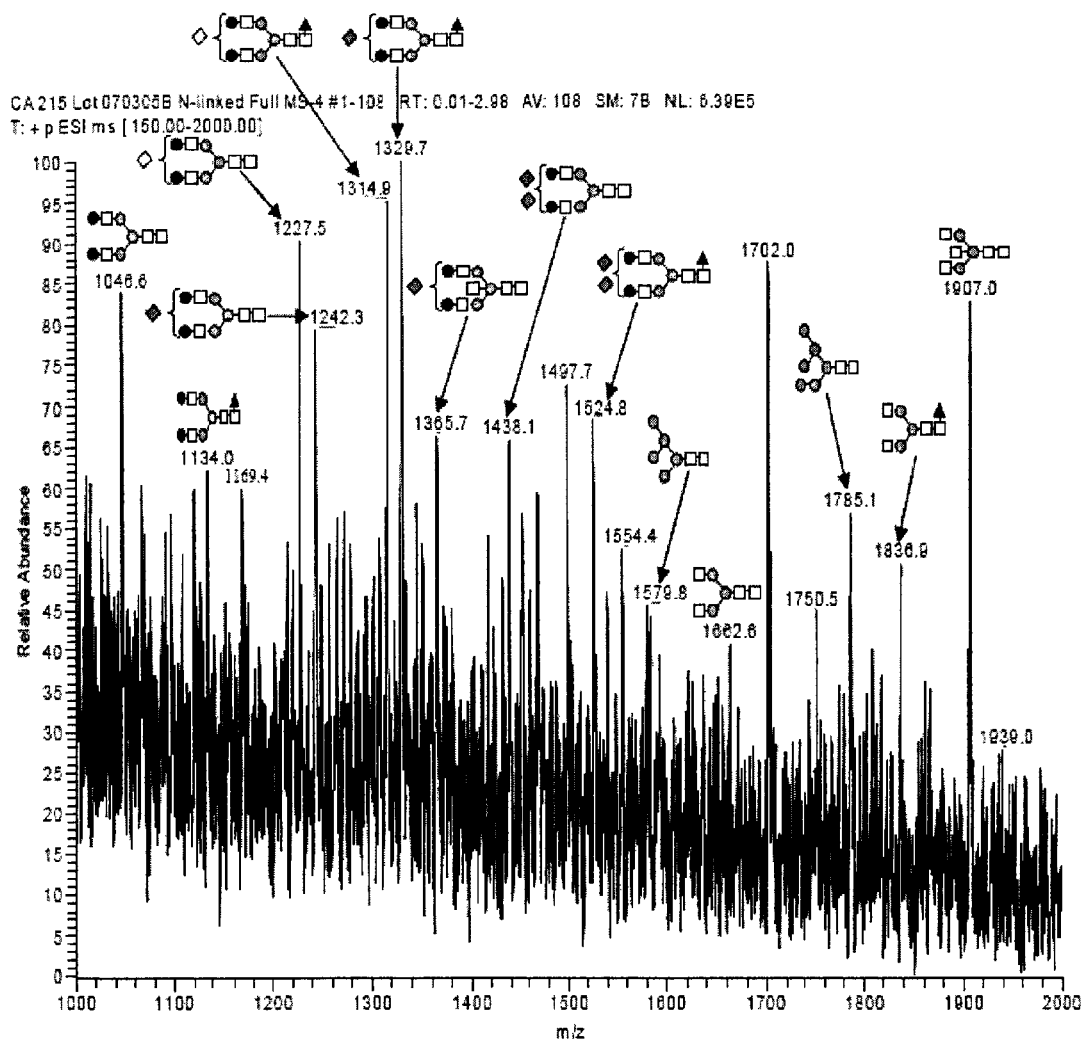
Figure 5:
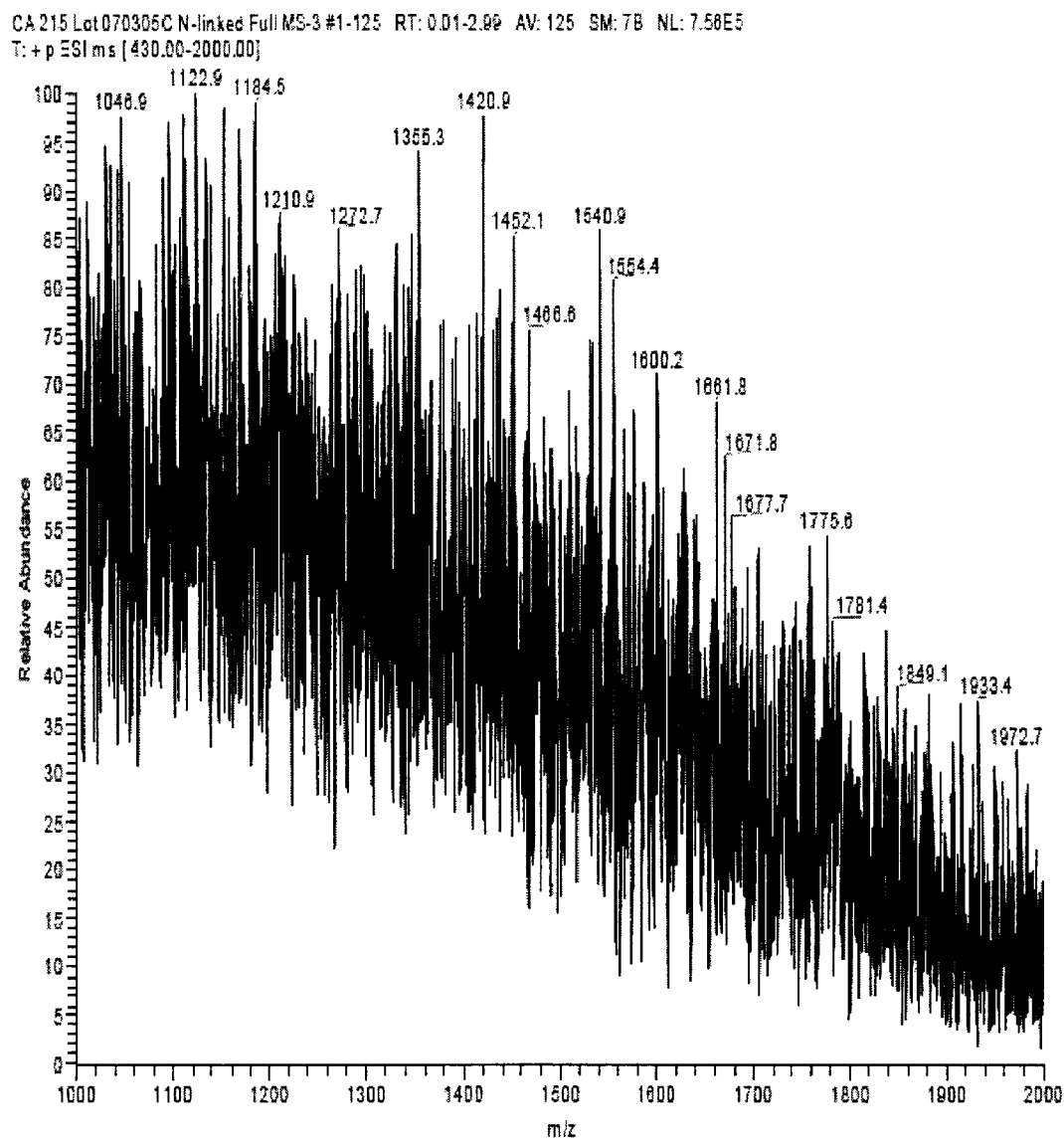

The present invention identifies the epitope on CA215 that is immunoreactive with monoclonal antibody RP215 as comprising the carbohydrate portion of this antigen and establishes the identity of the protein portion as a heavy chain immunoglobulin-like molecule, including the immunoglobulins of classes IgG, IgA and IgM. Although some light chain immunoglobulin-like moieties appear to be associated with CA215, they are not present in a 1:1 ratio to heavy chain as in ordinary immunoglobulins and do not bear the carbohydrate-containing epitope associated with the heavy chain-like portion. CA215 exists as undefined aggregates on the cancer cell surface.

The identification of the epitope recognized by RP215 comprising a carbohydrate not present on immunoglobulins in general and associated with the variable region of a heavy chain immunoglobulin-like molecule permits the production of more sophisticated immunogenic compositions which in turn are useful to inhibit the growth of tumor cells that display CA215 at their surfaces and to generate additional antibodies useful as detection reagents or immunotoxins. As demonstrated in the examples below, using the effective epitope of CA215, which, as stated above, is present on approximately 60% of human cancers, more effective immunogenic compositions can be formulated for cancer prevention and treatment.

Thus, rather than employ the entire CA215 antigen as a vaccine to slow the progression of cancer already established or to prevent the appearance of detectable amounts of cancer cells that express this antigen, only the portion of CA215 that bears the epitope relevant to detection and treatment need be employed.

As demonstrated below, the epitope consists essentially of a portion of the antigen which does not immunoreact with anti-human IgG, anti-human IgA, or anti-human IgM. The carbohydrate epitope has a composition distinct from that of these human immunoglobulins and distinct from that of the monoclonal antibody RP215 that immunoreacts with it. The composition of the carbohydrate epitope is approximately 1-3% fucose, 9-15% N-acetyl galactosamine, 27-30% N-acetyl glucosamine, 6-15% glucose, and 47-51% mannose. These are approximate figures, ± at least 1-2% in the latter four cases. The carbohydrate epitope is free of N-acetyl neuraminic acid and N-glycol neuraminic acid.

The epitope may also comprise at least a small portion of the variable region immunoglobulin heavy chain-like protein to which the carbohydrate is bonded.

Thus, the purified antigen CA215 has been identified as an immunoglobulin heavy chain-like molecule wherein the epitope portion immunoreactive with RP215 includes the carbohydrate associated with this amino acid sequence. By "immunoglobulin heavy chain-like molecule" is meant a molecule that includes an amino acid sequence that is able to confer immunoreactivity with anti-immunoglobulin antibodies. Thus, in the present case, CA215 is immunoreactive with anti-IgG, anti-IgA, and anti-IgM. The epitope immunoreactive with RP215, however, is not immunoreactive with anti-IgG, anti-IgA or anti-IgM. The amino acid sequence of the protein portion of CA215, thus, is sufficiently homologous with an immunoglobulin heavy chain that immunoreactivity is exhibited with respect to anti-heavy chain immunoglobulin antibodies. CA215 is also immunoreactive with antibodies that recognize immunoglobulin light chain. Thus, more generally, CA215 might be described simply as an immunoglobulin-like molecule.

The identified epitopes of the invention may be formulated into vaccines for administering to subjects for the treatment and prevention of cancer. Animal model subjects, such as mice, rats, rabbits, guinea pigs, and the like, may be administered such vaccines to optimize the formulation and protocols. Human subjects may be treated with additional therapies such as radiation and chemotherapy along with the immunogenic compositions of the invention.

Immunohistochemical staining studies of normal and cancerous tissues have demonstrated that the epitope identified herein is present on a number of types of human cancers, with varying levels of staining intensity. The epitope shows very intense staining on human cancers of the ovary, cervix, endometrium, colon, stomach, intestine, esophagus, breast, and lung. As noted herein, the tumor tissues from any particular subject can be evaluated using immunostaining for the presence and level of this epitope, thus providing information useful in the design of suitable vaccines, whether composed of the epitope itself or an antiidiotype antibody that mimics it as further described below.

In addition, to the use of the epitopes of the invention to generate antibodies endogenously in cancer-bearing subjects, the epitopes may also be used to generate additional antibodies useful in detection and themselves useful in treatment. As used herein, "antibodies" includes complete immunoglobulins as well as immunospecific fragments thereof, such as Fab, $Fab_{2'}$ and $F_v$ fragments. The antibodies may be monoclonal, prepared by standard and well known techniques and under these circumstances may be manipulated recombinantly to obtain humanized forms, chimeric forms in which the variable region associated with one species is coupled to a constant region associated with another or may be single-chain antibodies. Techniques for manipulation of monoclonal antibodies using the tools of recombinant production are well established. The epitopes of the invention may also be used as purification and identification tools for suitable antibodies.

In any of the immunogenic compositions, whether for the purpose of preparing monoclonal or polyclonal antibodies for diagnostic use or as a vaccine formulation, suitable adjuvants may be included in the composition, such as Freund's incomplete adjuvant, alum, and a multiplicity of other adjuvants well known in the art. In addition, the epitope may be coupled to additional moieties such as KLH or tetanus toxoid in order to enhance its immunogenicity. Thus, fusion proteins of the epitopes of the invention with additional heterologous protein are included in the scope of the invention.

The antibodies generated in response to the defined epitopes of the present invention can be labeled with radioisotopes, fluorophores, and in the case of in vitro assays, enzymes, and used to detect the presence of cancer cells. They may also be coupled to toxins for use in therapy.

In addition to the use of the defined epitope of the invention to prepare immunogenic formulations, antiidiotype antibodies which mimic this epitope may be isolated from subjects immunized with RP215 or immunogens that recognize the same epitope as does RP215. Antiidiotype monoclonal antibodies are obtained by immunizing mice or other suitable subjects with purified RP215 mAb or its Fab fragments (or with its humanized form) to elicit an antiidiotypic response against epitopes in the variable region. For example, BALB/C mice may be used. Conventional preparation of monoclonal antibodies by cell fusion and screening using RP215 or its Fab fragments or other moieties that recognize the epitope of the invention will identify monoclonal antibodies that are antiidiotypes. These antiidiotype mAb's then can serve as immunogens to elicit antibodies in subjects to target cancer cells. Thus, the antiidiotype antibodies can be substituted for the CA215 epitope as cancer therapy and in other applications.

Suitable formulations for the defined epitope of the invention are those conventional for immunogenic compositions and are found, for example, in Remington's Pharmaceutical Sciences, latest edition, Mack Publishing Co., Easton, Pa., incorporated herein by reference. Protocols for administration are dependent on the nature of the condition, the judgment of the attending physician, and the severity of the malignancy. Optimization of such protocols on a group or individual basis is well within ordinary skill.

The identification of the CA215 epitope as residing on an immunoglobulin-like moiety has led to improvements in immunoassays for this antigen. Previously, monoclonal RP215 has been used as both members of the "sandwich" employed in standard immunoassays using a variety of labels for detection, including enzymes, radioisotopes and fluorescent molecules. This was possible because CA215 commonly exists in polymeric form and multiple copies of the same epitope are available. An improved form of the assay, however, employs, as one member of the sandwich, antibodies immunoreactive with human immunoglobulin, preferably IgG, so that monomeric forms of CA215 may also be detected.

Improvements are also contemplated in the structure of RP215 through manipulation of the nucleotide sequence encoding the variable region. Thus, RP215 may be humanized or otherwise modified to improve its immunospecificity. The humanized form of this antibody is particularly useful in therapeutic applications. Such humanized forms may be complete immunoglobulins, or may include only variable regions, such as Fab or $Fab_2$, portions or may be single chain $F_v$ antibodies produced recombinantly. Any immunospecific portion of RP215 may be modified so as not to raise an immune response in human subjects.

Such antibodies or fragments or modified forms may be coupled to additional biologically active moieties, such as antineoplastic agents including immunoglobulins or fragments thereof immunoreactive with undesirable growth factors. In these conjugates, the RP215 serves as a targeting agent, as well as an anti-tumor factor per se. Thus, these forms of RP215 may be coupled to antineoplastic agents, such as paclitaxel, rapamycin or fumagillin or to moieties that are inhibitors of growth factors or their receptors, such as anti-GNRH receptor, anti-EGF, anti-EGFR, anti-VEGF, anti-VEGFR, and the like.

As used herein, "antineoplastic agent" includes small molecules, such as those set forth above, as well as antibodies or fragments thereof directed against growth factors or the receptors for such growth factors. Thus "anti-growth factor" or "anti-growth factor receptor" refers to immunoglobulins or fragments thereof that are immunoreactive with these moieties.

In the improved protocols of the present invention, an initial step is diagnosis of the presence of malignancies characterized by epithelial cells by virtue of the presence of CA215 antigen in body fluids. Such fluids include sera, plasma, blood, urine, saliva, and the like. The detection can be performed using RP215 or the modified forms thereof described above. The modified assay of the invention may also be used.

Once a diagnosis is made, the location of the tumor may be ascertained by obtaining an image by injection, in the case of humans, of the humanized form of RP215 coupled to an imageable label, such as a radioisotope, fluorescent dye, or luminescent system. Fluorescent proteins may be employed as fusion proteins or otherwise linked to the antibodies. In addition, the antibodies may be used as targeting agents for cytotoxic agents for the treatment of these solid tumors.

The following examples are offered to illustrate but not to limit the invention.

EXAMPLE 1

Characterization of CA215 as an Immunoglobulin-Like Molecule in Both Secreted and Membrane-Bound Forms with an Epitope Comprising a Carbohydrate In this example, the immunoglobulin-like nature of CA215 was confirmed and it was demonstrated that this cancer-associated antigen is produced simultaneously in both secreted and membrane-bound forms with differing molecular weights. In addition, the epitope of CA215 which is immunoreactive with RP215 comprises a carbohydrate moiety.

CA215 was purified from the shed medium of cultured OC-3-VGH cancer cells using the methods described in U.S. Pat. No. 5,650,291 cited and incorporated by reference above.

$NH_2$-terminal amino acid sequence analysis of purified CA215 gave a sequence identical to that of normal human IgG (VELVESGA) (SEQ ID NO:1).

The immunoglobulin nature of CA215 was confirmed by Western blot assays. CA215 proteins were separated by, and transferred to, nitrocellulose membrane strips from SDS-PAGE of either OC-3-VGH cancer cell extract, shed medium, or affinity-purified CA215.

After direct incubation with enzyme-labeled RP215 or with alkaline phosphatase (ALP) labeled anti-human IgG, the nitrocellulose strips were incubated with substrates (Bio-Rad Labs) for color detection of protein bands. Indirect binding assays with nitrocellulose membrane strips were also performed using unlabeled RP215 or unlabeled anti-human Ig as primary antibody and enzyme labeled goat anti-mouse IgG or rabbit anti-goat IgG as second antibodies. The results of these extensive studies are summarized in Table 1.

TABLE 1

Western blot assays using various antibody probes to reveal molecular weight(s) of detected protein bands on nitrocellulose strips which were derived from those of cancer cell extract, cultured shed medium or purified CA215.

| Primary Antibody | Secondary Antibody | Source of nitrocellulose strips | Molecular wt of protein band(s) detected (kDa) | Relative Staining Intensity |
|---|---|---|---|---|
| RP215-HRP[a] | — | OC-3-VGH cancer cell | 55 | + |

TABLE 1-continued

Western blot assays using various antibody probes to reveal molecular weight(s) of detected protein bands on nitrocellulose strips which were derived from those of cancer cell extract, cultured shed medium or purified CA215.

| Primary Antibody | Secondary Antibody | Source of nitrocellulose strips | Molecular wt of protein band(s) detected (kDa) | Relative Staining Intensity |
|---|---|---|---|---|
| Anti-human IgG (Mab) | — | purified CA215 | 60 | ++ |
|  |  |  | 25 | + |
| RP215 (Mab) | goat anti-mouse IgG-ALP[a] | OC-3-VGH cancer cell | 53-70 (broad) | +++ |
|  | goat anti-mouse IgG-ALP | cultured shed medium | 50-54 | + |
|  | goat anti-mouse IgG-ALP | purified CA215 | 50-52 | ++ |
|  | goat anti-mouse IgG-ALP | purified CA215 after pepsin treatment | 50-60 | ++ |
|  |  |  | 24 | + |
| Anti-human IgG (Mab) | goat anti-mouse IgG-ALP | OC-3-VGH cancer cell | 55-70 | +++ |
|  |  |  | 28 | ++ |
|  | goat anti-mouse IgG-ALP | purified CA215 | 52-60 | ++ |
| Anti-human IgA (Mab) | goat anti-mouse IgG-ALP | OC-3-VGH cancer cell | 57-70 (broad) | ++ |
| Anti-human IgM (Mab) | goat anti-mouse IgG-ALP | OC-3-VGH cancer cell | 53-70 (broad) | ++ |
| Anti-human Ig light κ chain (Mab) | goat anti-mouse IgG-ALP | OC-3-VGH cancer cell | 46-53 (weak) | ++ |
|  |  |  | 20-27 | + |
| Anti-human light λ chain (Mab) | goat anti-mouse IgG-ALP | OC-3-VGH cancer cell | 56 (weak) | ++ |
|  |  |  | 23-32 | + |

[a]HRP—horseradish peroxidase ALP—alkaline phosphatase

Both direct and indirect Western Blot assays using RP215 for detection give the same protein band patterns regardless of whether the protein was cellular extract, shed medium or affinity purified CA215. A strong, broad protein band was observed at molecular weight of 60 kDa and a minor protein band was also detected at 90 kDa.

Anti-human IgG monoclonal antibody (γ-chain-specific) also gave broad protein band(s) of 60 kDa either in a direct assay with ALP-labeled goat anti-human IgG, or in an indirect assay using this antibody as a secondary marker. Anti-human IgG lambda and kappa light chain monoclonal antibodies, also recognize protein band(s) of lower molecular weight (25-30 kDa), although with a much lower staining intensity. Anti-human IgA and IgM monoclonal antibodies recognize the protein bands with similar molecular size of 60 kDa similar to those recognized by RP215 monoclonal antibody.

As shown, the relative concentration of cancer cell-derived IgG is significantly higher than that of human IgA or human IgM ($\leq$5-10% of IgG). Western blot of affinity purified CA215 before and after pepsin digestion showed that after pepsin digestion, the remaining Fab fragment(s) of CA215 can be detected at low molecular range (~30 kDa) by RP215 monoclonal antibody.

More direct evidence that CA215 in cancer cells cross-reacts with human IgG, human IgA or human IgM, and that unique epitope(s) recognized by RP215 exist in these cancer cell-derived immunoglobulin-like molecules was obtained as follows: Monoclonal anti-human IgG (Cox-100)*, anti-human IgA and anti-human IgM were coated separately on microwells according to standard procedures. Shed medium from OC-3-VGH cells was added to the wells and RP215-HRP was used as the detecting antibody. The sandwich immunoassays were performed in one-step at room temperature overnight with 1/200 RP215-HRP+10 ug/ml normal mouse IgG.

The results of this assay in Table 2 demonstrate the presence of human immunoglobulin-like molecules in cultured shed media of OC3-VGH cancer cells with various antibodies to human immunoglobulin molecules. ODs is the OD value of sample and ODn is the OD value of negative control (culture medium).

TABLE 2

| Coating Abs/Ag | Capturing Ab | $ODs_{650}/ODn_{650}$ |
|---|---|---|
| Cox-100 (anti-hIgG Mab) | RP215-HRP | 13.6 |
| Anti-hIgA Mab | RP215-HRP | 1.7 |
| Anti-hIgM Mab | RP215-HRP | 2.2 |

Additional data were obtained to demonstrate direct binding between various anti-immunoglobulin antibodies to CA215 present in OC-3-VGH cancer cells as shown in Table 3A. In this case the experiment was conducted as a secondary two-step ELISA with primary antibodies incubated with sample overnight at room temperature, followed by goat anti-body Anti-Mouse IgG-ALP, for 1 hour at 37° C. ODs is the OD value of sample and ODn is the OD value of corresponding normal mouse IgG concentration.

TABLE 3A

| Capturing Ab | $ODs_{405}/ODn_{405}$ |
|---|---|
| 1.25 ug/ml Anti-hIgG$_2$ mAb | 9.1 |
| 2.50 ug/ml Anti-hIgG$_3$ mAb | 1.4 |
| 1.125 ug/ml Cox-100 | 12.9 |
| 1.125 ug/ml RP-215 | 11.6 |
| 5.00 ug/ml Anti-hKappa Mab | 1.5 |
| 5.00 ug/ml Anti-hLamda Mab | 2.8 |

Further evidence that CA215 is an immunoglobulin-like molecule mimicking the heavy chain of IgG was obtained using homology analysis. Table 3B shows the results obtained by MALDI-TOF MS system analysis.

TABLE 3B

Amino Acid Sequence Homology Analysis of Tryptic Peptides of CA215 determined by MALDI-TOF MS

| Peptide Fragments | SEQ ID NO: | Sequence Homology (%) |
|---|---|---|
| 1. K.DVLTITLTPK.V | 2 | immunoglobulin heavy chain variable region (66%) |
| 2. K.APQVYTIPPK.E | 3 | immunoglobulin gamma heavy chain 3 (87%) |
| 3. R.VNSAAFPAPIEK.T | 4 | immunoglobulin gamma heavy chain 3 (88%) |
| 4. K.APQVYTIPPKEQMAK.D | 5 | Ig gamma-3 chain C region (Heavy chain disease protein) (62%) |
| 5. R.SVSELPIMHQDWLNGK.E | 6 | immunoglobulin heavy chain (72%) |
| 6. K.NTQPIMDTDGSYFVYSK.L | 7 | immunoglobulin gamma-1 heavy chain constant region (61%) |
| 7. K.SSGTSYPDVLK.C | 8 | immunoglobulin heavy chain variable region (64%) |
| 8. K.VCNYVSWIK.Q | 9 | immunoglobulin heavy chain (75%) |
| 9. RTLYLQMNSLR | 10 | immunoglobulin heavy chain variable region (100%) |
| 10. SLVVAAVAPDNRNPAFTTMGWLFLK | 11 | immunoglobulin heavy chain variable region (70%) |
| 11. GDRVTITWR | 12 | immunoglobulin heavy chain variable region (88%) |
| 12. GLSDSVRSCR | 13 | immunoglobulin heavy chain variable region (75%) |
| 13. TAKGSTGMEILLSTLENTK | 14 | immunoglobulin heavy chain variable region VH (61%) |
| 14. KVTCVVVDISKD | 15 | immunoglobulin heavy chain (88%) |
| 15. GPLCGCCPGRSSQK | 16 | immunoglobulin variable region (43%) |
| 16. AELGGLLSPR | 17 | immunoglobulin heavy-chain subgroup VIII V-D-J region (85%) |
| 17. DGSISILGSDDATTCHIVVLR | 18 | immunoglobulin heavy chain variable region (100%-7/7) |
| 18. RTLYLQMNSLR | 19 | immunoglobulin heavy chain variable region (100%) |
| 19. KCELNCQAMGYR | 20 | immunoglobulin gamma chain, V region (85%) |
| 20. LSGSCRSTDSLHPCPPTALPR | 21 | immunoglobulin heavy chain variable region (33%) |
| 21. APTVVLMMTK | 22 | immunoglobulin heavy chain variable region (85%-5/6) |
| 22. ATSRGCITIIGGGDTATCCAK | 23 | immunoglobulin heavy chain variable region (69%-9/13) |
| 23. MSTRYHQAASDSYLELIK | 24 | immunoglobulin heavy chain variable region (87%-7/8) |
| 24. SLPGSPKDSSHLLSPLR | 25 | Ig heavy chain (VH4) V region (VDJ) |
| 25. GGNSGGSSSICYVLLGFIGTSK | 26 | immunoglobulin heavy chain VJH1 region (77%) |
| 26. AEDTAVYYCAKTLTIR | 27 | immunoglobulin heavy chain variable region (100%) |
| 27. GLECIGYMYSSGSSFYNPSLKSR | 28 | immunoglobulin heavy chain variable region (100%) |
| 28. MAYLQQTLAGPSGTR | 29 | immunoglobulin heavy chain variable region (88%-8/9) |
| 29. KGHQDSCPFELTACPNEGCTSQVPR | 30 | Ig heavy chain variable region (75%-6/8) |
| 30. GLEWVSAVSGSGTTTYYADSVK | 31 | immunoglobulin heavy chain variable region (91%) |
| 31. LSSVTAADTNVYYCAR | 32 | immunoglobulin heavy chain VHDJ region (93%) |
| 32. AETLVFSTHAVISMR | 33 | immunoglobulin heavy chain variable region (70%-7/10) |

Thus, sequences contained in CA215 are homologous to sequences in human immunoglobulin heavy chain.

In Table 3C, partial amino acid sequences of CA215 were mapped with the known sequences of human immunoglobulin heavy chains of several other cancer cells or tissues reported previously. It is now clearly established that CA215 is not a single well-defined molecule, but a mixture of numerous human immunoglobulin heavy chain molecules (e.g., IgG, IgA, IgM and numerous variations in the V regions). A unique character in these immunoglobulin mixtures is the existence of specific carbohydrate-associated epitope that can be commonly recognized by RP215 monoclonal antibody.

TABLE 3C

Comparisons of Partial Amino Acid Sequences of CA215 Deduced from MALDI-TOF MS with Those of Known Human Ig Heavy Chain from Cancer Cells

|   | FR1 | SEQ ID NO: | CDR1 | SEQ ID NO: |
|---|---|---|---|---|
| T47D (IgG) | EVQLVESGGGLVQPGGSLRLSCAASRFSSR | 34 | TSGMR | 35 |
| ZR75-1 (IgM) | EVQLVQSGAEVKKPGESLKISCKGSGYSFT | 36 | SYWIG | 37 |
| ZR75-1 (IgG) | EVQLLESGGGLVQPGGSLRLSCTASGFNFN | 38 | TYAMT | 39 |
| SKBR3 (IgG) | QVQLQESGPGLVKPSQTLSLTCTVSGGSVS | 40 | SGYYYWS | 41 |
| SKBR3 (IgA) | EVQLVESGGGLVQPGGSLTLSCAVSGLSFS | 42 | SSGMN | 43 |
| MDA-MB-231 (IgM) | EVQLVESGGGLVQPGGSLRLSCAASGFTFS | 44 | SYWMD | 45 |
| LUNG CANCER | EVQLEESGAEVKKPGESLKISCEASGYTFG | 46 | TYWIG | 47 |
| CA215 | KSSGTSYPDVLKC KVCN---- | 48 | YVSW | 49 |
|  | (SLVVAAVAPDNRNPAFT?) | 50 | (TMG?) |  |
|  | (ATSRGCITIIGGGDTATCCAK?) | 51 |  |  |
|  | (MAYLQQTLAGPSGTR?) | 52 |  |  |

|   | FR2 | SEQ ID NO: | CDR2 | SEQ ID NO: |
|---|---|---|---|---|
| T47D (IgG) | WVRQAPGKELEVA | 53 | PFWNGGSQKYCADSVT | 54 |
| ZR75-1 (IgM) | WVRQMPGKGLEWMG | 55 | I IYPGDSDTRYSPSFQG | 56 |
| ZR75-1 (IGG) | WVRQAPGKGLEWVS | 57 | T IAADGTWTSNADFVRG | 58 |
| SKBR3 (IgG) | RIRQHPGKGLEWIG | 59 | YIYYNGSTYENPSLKS | 60 |
| SKBR3 (IgA) | WVRQASGKGLEWVG | 61 | RIGSKAASDTTSYAASVRG | 62 |
| MDA-MB-231 (IgM) | WVRQVPGKGLVWVS | 63 | RISPDGRTTTYADSVEG | 64 |
| LUNG CANCER | WVRQMPGKGLEWMG | 65 | I IYPGDSDTTY SPSFRG | 66 |
| CA215 | IKQ------- GLEWVS | 67 | AVSGSGTTTYYADSVK | 68 |
|  | (WLFLK?) | 69 | YMYSSGSSFYNPSLKSR?) G | 71 |
|  | (GLECIG | 70 |  |  |

|   | FR3 | SEQ ID NO: | CDR3 | SEQ ID NO: |
|---|---|---|---|---|
| T47D (IgG) | GRFTFSETFLRPCSLCKCTVNLRARPS I PAP | 72 | GITVPHPRLCPRN | 73 |
| ZR75-1 (IgM) | QVTISADKSISTAYLQWSSLKASDTAMYYCAR | 74 | QEIVAFS | 75 |
| ZR75-1 (IgG) | RLTISRDNSRNTLYLQMNSLRAEDTAIYFCAK | 76 | DWYDY | 77 |
| SKBR3 (IgG) | RASISVDTSKNQFSLKLSSVTAADTAVYYCAR | 78 | DIKHTYGPN | 79 |
| SKBR3 (IgA) | RFFISRDDSKKTVYLQMNSLKTEDTAVYYCSR | 80 | QGCGGDCHIPKM | 81 |
| MDA-MB-231 (IgM) | RFTISRDNAKNTLYLQMNSLRAEDTAVYYCAG | 82 | GYLSSH | 83 |
| LUNG CANCER | QVTLSVDKFINTAYLQWDSLKASDTAIYYCAR | 84 | WDVMIGFYTA | 85 |
| CA215 | DRVTITWR RTLYLQMNSLRAEDTAVYYCAK | 86 | TLTIR | 87 |
|  | (LSSVTAADTNVYYCAR?) | 88 |  |  |
|  | (MAYLQQTLAGPSGTR?) | 89 |  |  |

|   | JH | SEQ ID NO: | CH | SEQ ID NO: |
|---|---|---|---|---|
| T47D (IgG) | YFDSGQGTLVTVSS | 90 | ASTKGPSVFPL | 91 |
| ZR75-1 (IgM) | YYYMDVWGKGTTVTVSS | 92 | GSASPQPFSPS | 93 |
| ZR75-1 (IgG) | WGQGTLVTALL | 94 | TVSTGLHQGPIGLPP | 95 |
| SKBR3 (IgG) | YNCYMDVWGKGTTVTVSS | 96 | GLHQGPIGLPP | 97 |
| SKBR3 (IgA) | YYYYGMDVWGQGTTVTVSS | 98 | ASPTSPKVF | 99 |
| MDA-MB-231 (IgM) | DYWGRGTLVTVSS | 100 | GECIRPNPFPP | 101 |
| LUNG CANCER | DYWGQGTQVTVS | 102 | SASTKGPSVFPLAPSSKSTSGGTAVLGCLV | 103 |
|  |  |  | KDYFPEPVTV | 104 |
| CA215 |  |  | TAKGSTGMEILL STLENTK (?) | 105 |

CA215 (constant region)
----GNSGGSSSICYVLLGFIGTSKLSGSCRSTDSLHPCPPTALPRAELGGLLSPRKDVLTITLTPK VTCVVVDISKD--
---RSVSELPIMHQDWLNGKERVNSAAFPAPIEKTKAPQVYTIPPKEQMAKD----
----KGHQDSCPEELTACPNEGCTSQVPRKNTQPIMDTDGSYFVYSKL (SEQ ID NO: 106)

Note:
The following sequences cannot be mapped due to microheterogeneity: 1. GPLCGCCPGRSSQK (SEQ ID NO: 107); 2. APTVVLMMTK (SEQ ID NO:108); 3. 3MSTRYHQAASDSYLELIK (SEQ ID NO: 109); 4. SLPGSPKDSSHLLSPLR (SEQ ID NO: 110).

In Table 3D, comparisons of amino acid sequences of CA215 in the constant region deduced from MALDI-TOF MS and RT-PCR are presented together with that of anti-human colon carcinoma heavy chain from the GenBank.

TABLE 3D

Comparisons of amino Acid Sequences in the Constant Region among those of
CA215 deduced from RT-PCR and MALDI-TOF MS as well as those from Anti-
human Colon Carcinoma Heavy Chain (AHCCHC gb|AAB28159.1|)
(SEQ ID NOS: 111-113)

```
AHCCHC              PKDVLTITLTPKVTCVVVDISKDDPEVQFSWFVDDVEVHTAQTQPREEQF
CA215 by MALDI-TOF MS  KDVLTITLTPKVTCVVVDISKD.................. LSTLE
CA215 by RT-PCR     ............................... VEVHNAKTKPREEQF

AHCCHC              NSTFRSVSE LP I MHQDWLNGKEFKCRVNSAAFPAPIEKTISK TKG---------
CA215 by MALDI-TOF MS  N-TKRSVSE LP I MHQDWLNGKE...RVNSAAFPAPIEKT.......
CA215 by RT-PCR     NSTYRVVSVLTVVHQDWLNGKEYKCKVSNKGLPAPIEKTISKTKGGTRGC

AHCCHC              ------------------------RPKAPQVYT IPPPKEQMAKDKV
CA215 by MALDI-TOF MS  ...........................KAPQVYT IPP-KEQMAKDKV
CA215 by RT-PCR     EGHMDRGQLGPPSALGVTAVPTSVPTGQPREPQVYTLPPSREEMTKNQV

AHCCHC              SLTCMI TDFFPEDITVEWQWNGQPAENYKNTQPIMDTDGSYFVYSKL
CA215 by MALDI-TOF MS  --- TCVVVD-ISKD... ......... KNTQPIMDTDGSYFVYSKL
CA215 by RT-PCR     SLTCLVKGFYPSDIAVEWE SNGQPENNYK TT
```

The carbohydrate portion of CA215 was analyzed following verification of results demonstrating the ability of periodate to destroy the immunoreactivity of this antigen in a sandwich assay, thus establishing the presence of carbohydrate in the epitope. Verification was performed as follows:

PBS-washed OC-3-VGH cancer cells (conc. $1 \times 10^6$ cells/ml) were incubated with 100 mM $NaIO_4$ for 30 minutes, the cells were washed with PBS containing 0.5% BSA, and then dried on microwells at $1 \times 10^4$ cells/well. The cell-coated microwells were then blocked with 0.5% BSA in PBS and direct binding enzyme immunoassays using RP215 labeled with horseradish peroxidase (RP215-HRP) were performed at 37° C. for one hour followed by extensive washes and color development with TMB substrate. For comparison wells coated with cancer cells without $NaIO_4$ treatments served as control. The binding between RP215-HRP and cancer cell-coated wells treated with periodate was drastically reduced. In addition, the presence of 10 to 100 μg/ml goat anti-human IgG reduced the binding to RP215-HRP to the wells coated with cancer cells in a dose-dependent manner, indicating that goat anti-human IgG competes with RP215-HRP to bind the complete CA215 antigen. The results of this study are summarized in Table 4.

TABLE 4

Direct binding assays to reveal the effect of $NaIO_4$ treatment to OC-3-VGH cancer-cells on the binding of RP215-HRP to the cancer cell-coated wells as well as its binding inhibition in the presence of goat anti-human IgG

| | Optical Density at 450 nm | |
|---|---|---|
| Assay Conditions | Without $NaIO_4$ treatment | With $NaIO_4$ treatment |
| RP215-HRP (10 ug/ml) + normal mouse IgG (10 ug/ml) | 2.153 (100%)[a] | 0.797 (37%) |
| RP215-HRP (10 ug/ml) + normal mouse IgG (10 ug/ml) + goat anti-human IgG (20 ug/ml) | 0.961 (45%) | 0.333 (15%) |
| RP215-HRP (10 ug/ml) + normal mouse IgG (10 ug/ml) + goat anti-human IgG (50 ug/ml) | 0.471 (22%) | 0.252 (12%) |

TABLE 4-continued

Direct binding assays to reveal the effect of $NaIO_4$ treatment to OC-3-VGH cancer-cells on the binding of RP215-HRP to the cancer cell-coated wells as well as its binding inhibition in the presence of goat anti-human IgG

| | Optical Density at 450 nm | |
|---|---|---|
| Assay Conditions | Without $NaIO_4$ treatment | With $NaIO_4$ treatment |
| RP215-HRP (10 ug/ml) + normal mouse IgG (10 ug/ml) + goat anti-human IgG (100 ug/ml) | 0.163 (8%) | 0.158 (7%) |

[a]percent maximum binding

The presence of both secreted and membrane-bound forms of CA215 in OC-3-VGH cells was further confirmed as shown in Table 5 below, and in FIGS. 6 and 7. Table 5 shows the results of Western blot when the strips treated with detection reagents either contained immobilized OC-3-VGH whole cells, OC-3-VGH culture medium or purified antigen. As shown, regardless of the detection method, the purified antigen produced a result at only 54-55 kD molecular weight, as did the culture medium. However, the whole cells showed results at molecular weights of both 50-56 and 68-73 kD. In Table 5, N/A represents "not applicable" and ND represents "not done."

TABLE 5

Western Blot of OC-3-VGH cells, Culture Medium and Purified CA215 with RP215 and Anti-Human IgG Probes Under Reducing Conditions

| Western Blot Conditions | | Molecular weight of detected bands from various sources of nitrocellulose strips (KDa) | | |
|---|---|---|---|---|
| Primary Antibody | Secondary Antibody | OC-3-VGH whole cell strips | OC-3-VGH culture medium strips | Purified CA215 strips |
| RP215 | GAMIgG-ALP | 56/68 | 55 | 55 |
| MAHIgG | GAMIgG-ALP | 55-73 (broad) | 55 | 54 |

TABLE 5-continued

Western Blot of OC-3-VGH cells, Culture Medium and Purified CA215 with RP215 and Anti-Human IgG Probes Under Reducing Conditions

| Western Blot Conditions | | Molecular weight of detected bands from various sources of nitrocellulose strips (KDa) | | |
|---|---|---|---|---|
| Primary Antibody | Secondary Antibody | OC-3-VGH whole cell strips | OC-3-VGH culture medium strips | Purified CA215 strips |
| MAHIgA-ALP | N/A | 50 | ND | ND |
| MAHIgM-ALP | N/A | 70 | ND | ND |

Figure 6:
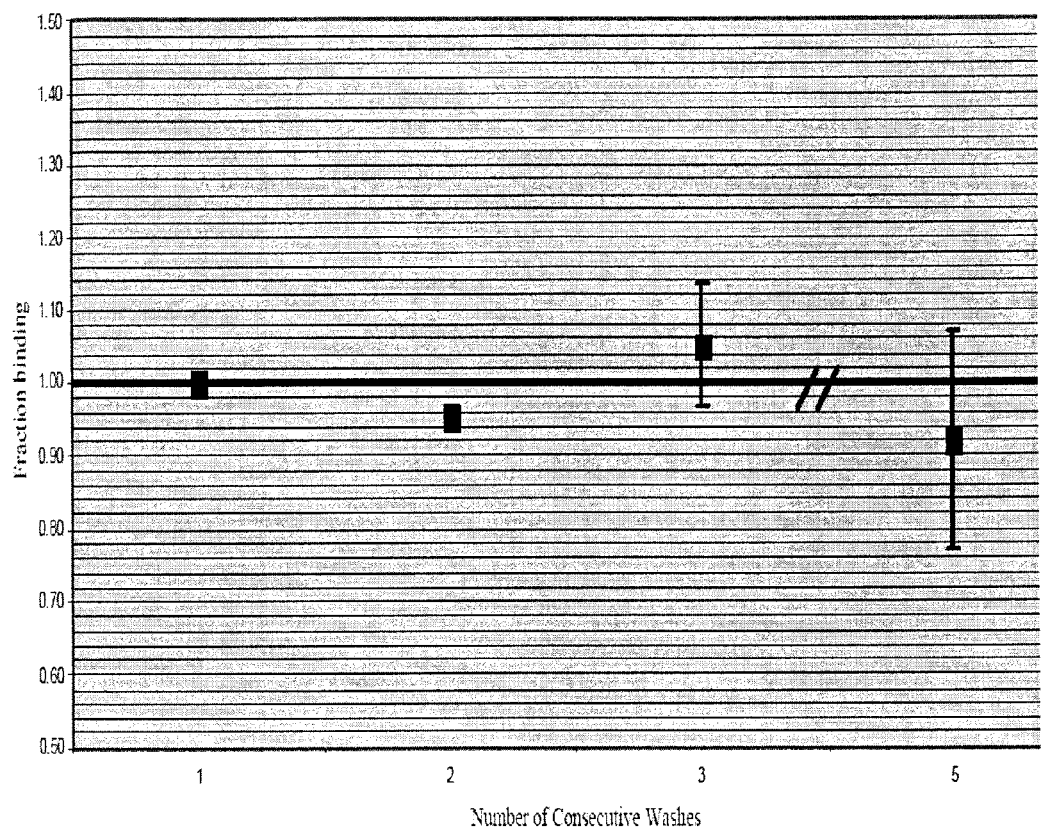
FIG. 6 shows the effect of washing on the presence of CA215 in membrane-bound form on OC-3-VGH cells.

FIG. 6 shows the result of consecutive PBS washes on the fraction of binding of RP215 to OC-3-VGH cells. As shown, even after five consecutive washes, no appreciable change in the fraction binding the cells occurs. These results were obtained on isolated OC-3-VGH cells not in culture.

Figure 7:
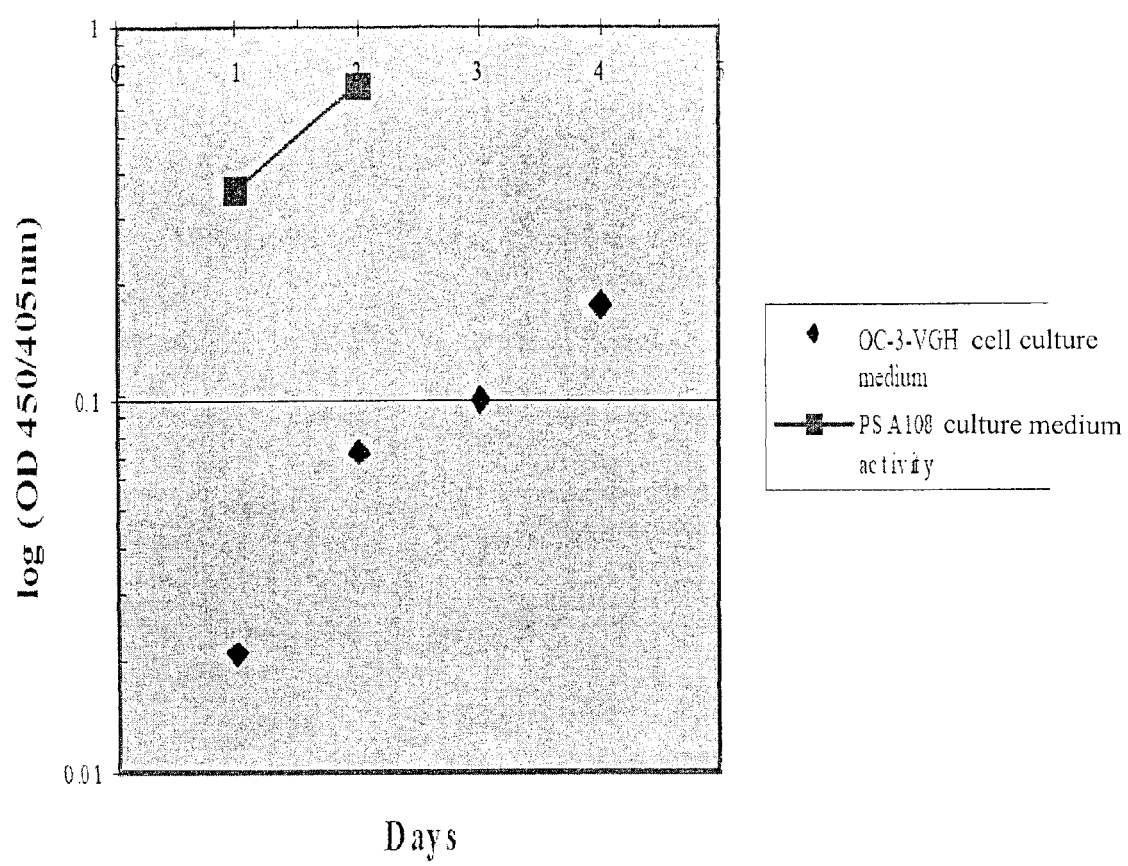
FIG. 7 shows the secretion pattern of the OC-3-VGH cell line compared to a hybridoma cell line with respect to the secreted form of CA215.

This is in contrast with the results in FIG. 7 which show that when culture medium is assessed from either OC-3-VGH cells or a comparable standard hybridoma secretion system, similar patterns of secretion are obtained based on absorbance at 450 nm using the HRP detection system.

Thus, the secreted and membrane-bound forms appear to be produced simultaneously and have differing molecular weights. The secreted form has a molecular weight of approximately 55 kD and the membrane-bound form has a molecular weight of approximately 73 kD.

EXAMPLE 2

Carbohydrate Composition of Affinity-Purified CA215

The carbohydrate composition of CA215 was analyzed through a contract service by Complex Carbohydrate Research Center (Athens, Ga., USA). For comparison, composition analyses of normal human IgG, and RP215 monoclonal antibody were also performed.

The results of this comparative carbohydrate composition analysis are summarized in Table 6. The values of glucose were not determined because glucose was identified as a major contaminant and thus not susceptible to accurate measurement.

TABLE 6

Neutral and Amino Sugar Composition (excluding glucose)

| Sample ID | Types of Amino-/Sugar | nmoles/µg | Molar % |
|---|---|---|---|
| Human IgG - Salt free | Fucose | 0.0077 | 7.93 |
| | N-acetyl-galactosamine | 0.0068 | 6.99 |
| | N-acetyl-glucosamine | 0.0394 | 40.72 |
| | Galactose | 0.0053 | 5.46 |
| | Glucose | ND | ND |
| | Mannose | 0.0376 | 38.90 |
| | N-acetyl-neuraminic acid | 0.0000 | 0.00 |
| | N-glycol-neuraminic acid | 0.0000 | 0.00 |
| | Total: | 0.0967 | 100.0 |
| RP215 Mab - Salt free | Fucose | 0.0085 | 5.03 |
| | N-acetyl-galactosamine | 0.0000 | 0.00 |
| | N-acetyl-glucosamine | 0.0762 | 45.16 |
| | Galactose | 0.0076 | 4.48 |
| | Glucose | ND | ND |
| | Mannose | 0.0765 | 45.33 |
| | N-acetyl-neuraminic acid | 0.0000 | 0.00 |
| | N-glycol-neuraminic acid | 0.0000 | 0.00 |
| | Total: | 0.1688 | 100.0 |
| CA215 Lot No. 070305 A | Fucose | 0.0018 | 1.10 |
| | N-acetyl-galactosamine | 0.0154 | 9.45 |
| | N-acetyl-glucosamine | 0.0442 | 27.05 |
| | Galactose | 0.0229 | 14.05 |
| | Glucose | ND | ND |
| | Mannose | 0.0789 | 48.35 |
| | N-acetyl-neuraminic acid | 0.0000 | 0.00 |
| | N-glycol-neuraminic acid | 0.0000 | 0.00 |
| | Total: | 0.1633 | 100.0 |
| CA215 Lot No. 070305 B | Fucose | 0.0018 | 2.46 |
| | N-acetyl-galactosamine | 0.0095 | 13.04 |
| | N-acetyl-glucosamine | 0.0208 | 28.40 |
| | Galactose | 0.0042 | 5.68 |
| | Glucose | ND | ND |
| | Mannose | 0.0369 | 50.41 |
| | N-acetyl-neuraminic acid | 0.0000 | 0.00 |
| | N-glycol-neuraminic acid | 0.0000 | 0.00 |
| | Total: | 0.0731 | 100.0 |

Normal human IgG and RP215 (mouse IgG) have similar carbohydrate compositions, though human Ig contains N-acetyl galactosamine, which is absent from RP215. CA215 exhibits different sugar content from either normal human or mouse IgG. CA215 contains lower percentage of N-acetyl-glucosamine (27-28% vs. 40-45%) but a significantly higher amount of mannose (48-50% vs. 38-45%).

EXAMPLE 3

N-Linked and O-Linked Oligosaccharide Profiling

In addition to overall carbohydrate content, the structures of N-linked glycans associated with human IgG, RP215, and CA215 were determined by electrospray ionization mass spectrometry (ESI-MS).

In carrying out this determination, the samples were dissolved in 1 mL of nanopure water. Eight hundred microliters of each of human IgG, RP215 mAb, and CA215 sample B, 900 µL of CA215 sample A and all of CA215 sample C were pipetted into screw-cap tubes and lyophilized. The dried samples were dissolved with 100 µL ammonium bicarbonate buffer (50 mM, pH 8.4) and followed immediately by reduction with 25 mM dithiothreitol (45 min at 50° C.) and carboxyamidomethylation with 90 mM iodoacetamide (45 min at room temperature in the dark) prior to trypsin digestion (37° C., overnight). A second enzyme, peptide N-glycosidase F (New England BioLabs) was added to each of the tryptic digests and incubated at 37° C. for 18 hours to release the N-linked glycans. After enzymatic digestions, the samples were passed through a C18 reversed phase cartridge. The N-linked glycans from each sample were eluted with 5% acetic acid and then lyophilized.

The lyophilized N-linked fraction of each sample was dissolved in dimethylsulfoxide and then methylated with NaOH and methyl iodide. The reaction was quenched by addition of water, and per-O-methylated carbohydrates were extracted with dichloromethane. The organic phase was concentrated to dryness and then dissolved with methanol for glycan structural analysis.

The profiles of N-linked glycans from all five samples were analyzed by electrospray ionization mass spectrometry (ESI-MS) using an LCQ-MS (Thermo Finnigan) quadrupole ion trap. Each sample (~5 pmol/μL) was infused directly into the instrument at a constant flow rate of 1 μL/min via a syringe pump (Harvard Apparatus) and sprayed at 3.5 kV. A normalized collision energy of 35 and an isolation mass window of 2 Da was applied to obtain MSn.

The results are shown in Tables 7-10 and FIGS. 1-5. No table is provided for CA215 sample C, as apparently the sample was too small and defined peaks could not be obtained. In Tables 9 and 10, the highlighted areas represent structures that are found in CA215, but not in IgG or RP215.

In addition, it appears that sialic acids were not detected, again, possibly due to low sample size.

TABLE 7

Profile of N-linked glycans of human IgG by ESI-MS

| Observed Mass {M + Na} | Charge state | Proposed Structure | Structure |
|---|---|---|---|
| 1032 | double | $GlcNAc_4Man_3Hex_1Fuc_1$ | 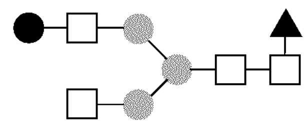 |
| 1134 | double | $GlcNAc_4Man_3Hex_2Fuc_1$ | 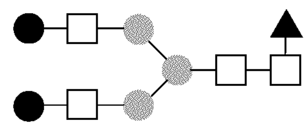 |
| 1228 | double | $GlcNAc_4Man_3Hex_2NeuAc_1$ | 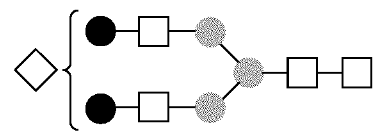 |
| 1257 | double | $GlcNAc_5Man_3Hex_2Fuc_1$ | 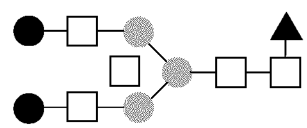 |
| 1315 | double | $GlcNAc_4Man_3Hex_2Fuc_1NeuAc_1$ | 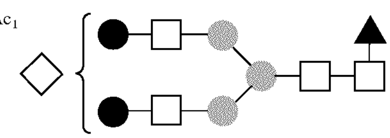 |
| 1350 | double | $GlcNAc_5Man_3Hex_2NeuAc_1$ | 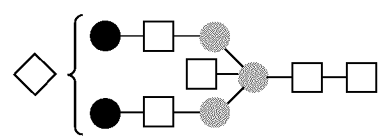 |
| 1408 | double | $GlcNAc_4Man_3Hex_2NeuAc_2$ | 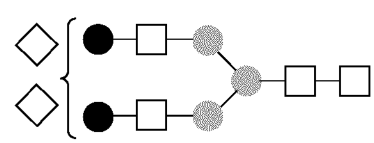 |
| 1437 | double | $GlcNAc_5Man_3Hex_2Fuc_1NeuAc_1$ | 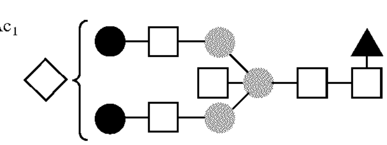 |
| 1495 | double | $GlcNAc_4Man_3Hex_2Fuc_1NeuAc_2$ | 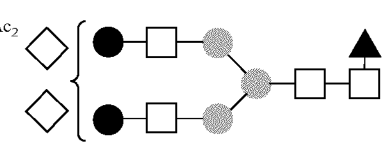 |

TABLE 7-continued

Profile of N-linked glycans of human IgG by ESI-MS

| Observed Mass {M + Na} | Charge state | Proposed Structure | Structure |
|---|---|---|---|
| 1618 | double | $GlcNAc_5Man_3Hex_2Fuc_1NeuAc_2$ | 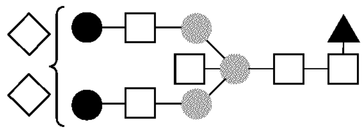 |
| 1836 | single | $GlcNAc_4Man_3Fuc_1$ | 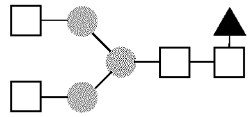 |
| 1866 | single | $GlcNAc_4Man_3Hex_1$ | 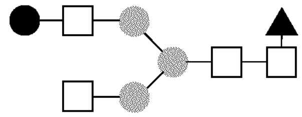 |
| 1907 | single | $GlcNAc_5Man_3$ | 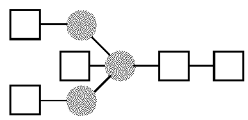 |

Legend:
- Mannose
- Galactose
- ▲ Fucose
- ☐ N-acetyl glucosamine
- ◇ N-acetyl neuraminic acid

TABLE 8

Profile of N-linked glycans of RP 215 Mab by ESI-MS

| Observed Mass {M + Na} | Charge state | Proposed Structure | Structure |
|---|---|---|---|
| 1032 | double | $GlcNAc_4Man_3Hex_1Fuc_1$ | 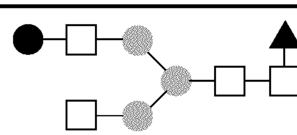 |
| 1134 | double | $GlcNAc_4Man_3Hex_2Fuc_1$ | 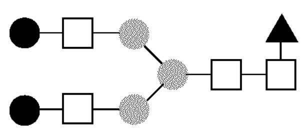 |
| 1242 | double | $GlcNAc_4Man_3Hex_2NeuGc_1$ | 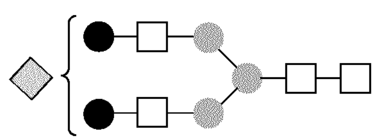 |
| 1314 | double | $GlcNAc_4Man_3Hex_2Fuc_1NeuAc_1$ | 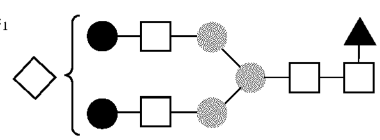 |
| 1453 | double | $GlcNAc_5Man_3Hex_2Fuc_1NeuGc_1$ | 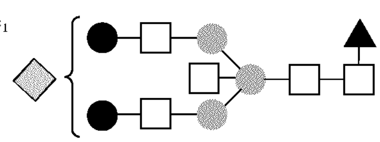 |

TABLE 8-continued

Profile of N-linked glycans of RP 215 Mab by ESI-MS

| Observed Mass {M + Na} | Charge state | Proposed Structure | Structure |
|---|---|---|---|
| 1417 | single | $GlcNAc_3Man_3$ | 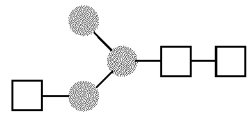 |
| 1663 | single | $GlcNAc_4Man_3$ | 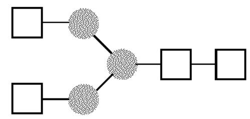 |
| 1836 | single | $GlcNAc_4Man_3Fuc_1$ | 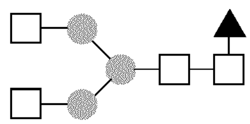 |
| 1866 | single | $GlcNAc_4Man_3Hex_1$ | 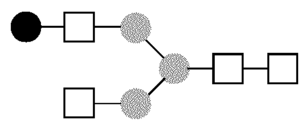 |

Legend:
- Mannose
- Galactosze
- ▲ Fucose
- ☐ N-acetyl glucosamine
- ◇ N-acetyl neuraminic acid
- ◇ N-glycol neuraminic acid

TABLE 9

Profile of N-linked glycans of CA215 Sample A by ESI-MS

| Observed Mass {M + Na} | Charge state | Proposed Structure | Structure |
|---|---|---|---|
| 1047 | double | $GlcNAc_4Man_3Hex_2$ | 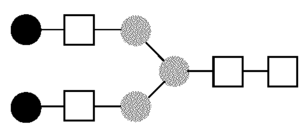 |
| 1172 | single | $GlcNAc_2Man_3$ | 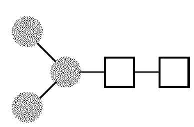 |
| 1228 | double | $GlcNAc_4Man_3Hex_2NeuAc_1$ | 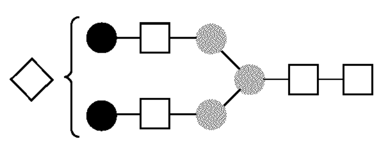 |
| 1243 | double | $GlcNAc_4Man_3Hex_2NeuGc_1$ | 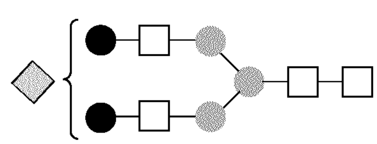 |

TABLE 9-continued

Profile of N-linked glycans of CA215 Sample A by ESI-MS

| Observed Mass {M + Na} | Charge state | Proposed Structure | Structure |
|---|---|---|---|
| 1330 | double | $GlcNAc_4Man_3Hex_2Fuc_1NeuGc_1$ | 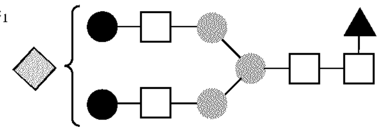 |
| 1452 | double | $GlcNAc_5Man_3Hex_3NeuAc_1$ | 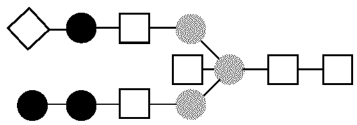 |
| 1467 | double | $GlcNAc_5Man_3Hex_3NeuGc_1$ | 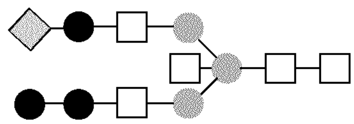 |
| 1418 | single | $GlcNAc_3Man_3$ | 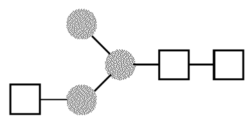 |
| 1621 | single | $GlcNAc_3Man_3Hex_1$ | 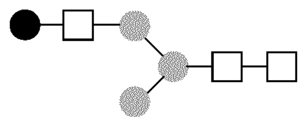 |
| 1663 | single | $GlcNAc_4Man_3$ | 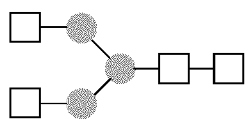 |
| 1836 | single | $GlcNAc_4Man_3Fuc_1$ | 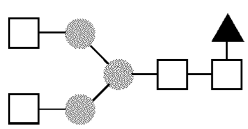 |
| 1866 | single | $GlcNAc_4Man_3Hex_1$ | 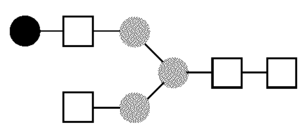 |
| 1907 | single | $GlcNAc_5Man_3$ | 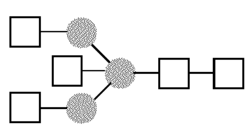 |

Legend:
- Mannose
- Galactose
- ▲ Fucose
- ☐ N-acetyl glucosamine
- ◇ N-acetyl neuraminic acid
- ◇ N-glycol neuraminic acid

TABLE 10

Profile of N-linked glycans of CA215 Sample B by ESI-MS

| Observed Mass {M + Na} | Charge state | Proposed Structure | Structure |
|---|---|---|---|
| 1047 | double | GlcNAc$_4$Man$_3$Hex$_2$ | 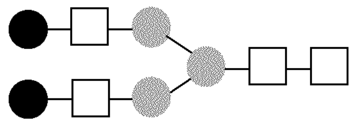 |
| 1134 | double | GlcNAc$_4$Man$_3$Hex$_2$Fuc$_1$ | 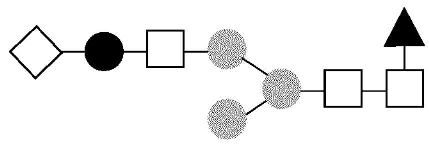 |
| 1169 | double | GlcNAc$_5$Man$_3$Hex$_2$ | 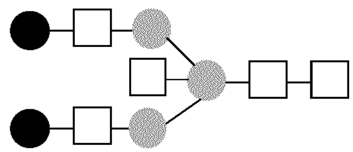 |
| 1228 | double | GlcNAc$_4$Man$_3$Hex$_2$NeuAc$_1$ | 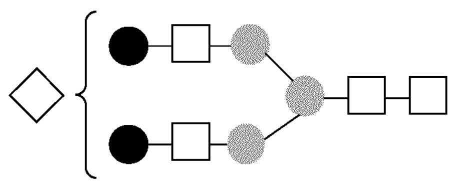 |
| 1242 | double | GlcNAc$_4$Man$_3$Hex$_2$NeuGc$_1$ | 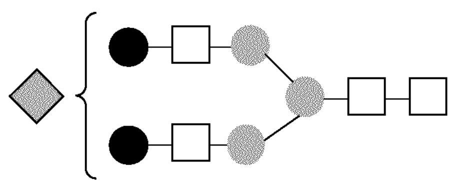 |
| 1315 | double | GlcNAc$_4$Man$_3$Hex$_2$Fuc$_1$NeuAc$_1$ | 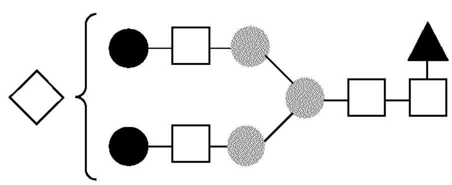 |
| 1330 | double | GlcNAc$_4$Man$_3$Hex$_2$Fuc$_1$NeuGc$_1$ | 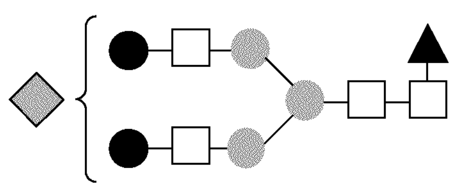 |
| 1366 | double | GlcNAc$_5$Man$_3$Hex$_2$NeuGc$_1$ | 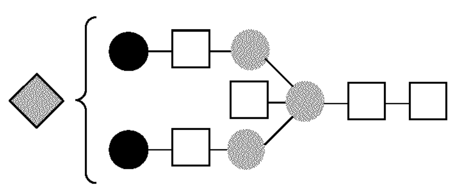 |

TABLE 10-continued

Profile of N-linked glycans of CA215 Sample B by ESI-MS

| Observed Mass {M + Na} | Charge state | Proposed Structure | Structure |
|---|---|---|---|
| 1438 | double | $GlcNAc_4Man_3Hex_2NeuGc_2$ | 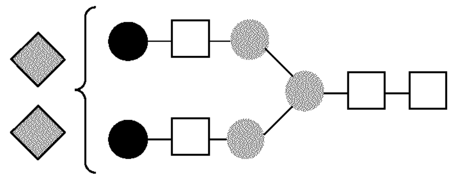 |
| 1525 | double | $GlcNAc_4Man_3Hex_2Fuc_1NeuGc_2$ | 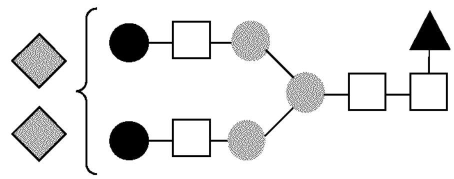 |
| 1580 | single | $GlcNAc_2Man_5$ | 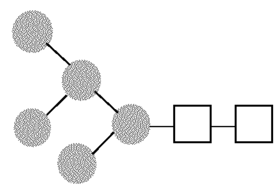 |
| 1663 | single | $GlcNAc_4Man_3$ | 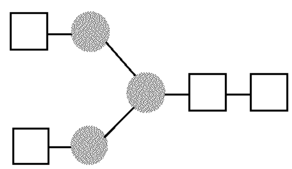 |
| 1785 | single | $GlcNAc_2Man_6$ | 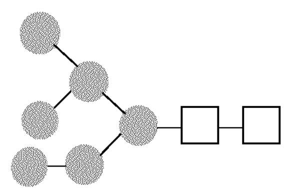 |
| 1837 | single | $GlcNAc_4Man_3Fuc_1$ | 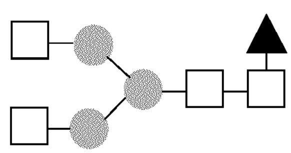 |
| 1907 | single | $GlcNAc_5Man_3$ | 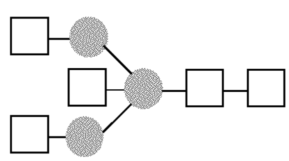 |

Legend:
- Mannose
- Galactose
- ▲ Fucose
- □ N-acetyl glucosamine
- ◇ N-acetyl neuraminic acid
- ◆ N-glycol neuraminic acid Generally, in both human IgG and RP215, the major ion detected has a glycosylated structure (N/Z 1836). Although this was also detected in the CA215 samples, the signal was not as dominating as in human IgG and RP215. Other fucosylated and sialylated glycans were detected in all samples.

In addition, the O-linked sugar content of these materials was also determined with the results shown in Table 11.

TABLE 11

Monosaccharide Composition of O-glycans Analyzed by HPAEC.

| Sample name | Analyte | nmoles | Molar percentage |
|---|---|---|---|
| Human IgG - Sigma | Fucose | 0.0702 | 4.1 |
| | N-acetyl-galactosamine | 0.3360 | 19.7 |
| | N-acetyl-glucosamine | 0.7958 | 46.8 |
| | Galactose | 0.3717 | 21.8 |
| | Glucose | nd | nd |
| | Mannose | nd | nd |
| | N-acetyl-neuraminic acid | 0.1276 | 7.6 |
| | N-glycol-neuraminic acid | nd | nd |
| | Total | 1.7013 | 100.0 |
| RP215 Mab # 070801-A | Fucose | 0.0692 | 6.2 |
| | N-acetyl-galactosamine | 0.2004 | 18.1 |
| | N-acetyl-glucosamine | 0.3569 | 32.2 |
| | Galactose | 0.3475 | 31.4 |
| | Glucose | nd | nd |
| | Mannose | nd | nd |
| | N-acetyl-neuraminic acid | 0.0838 | 7.6 |
| | N-glycol-neuraminic acid | 0.0501 | 4.5 |
| | Total | 1.1079 | 100.0 |
| CA215 1 # 070801-1 | Fucose | 0.0981 | 14.8 |
| | N-acetyl-galactosamine | 0.0961 | 14.5 |
| | N-acetyl-glucosamine | 0.1371 | 20.7 |
| | Galactose | 0.1473 | 22.3 |
| | Glucose | nd | nd |
| | Mannose | nd | nd |
| | N-acetyl-neuraminic acid | 0.1320 | 20.0 |
| | N-glycol-neuraminic acid | 0.0508 | 7.7 |
| | Total | 0.6614 | 100.0 |
| CA215 4 # 070801-4 | Fucose | nd | nd |
| | N-acetyl-galactosamine | nd | nd |
| | N-acetyl-glucosamine | nd | nd |
| | Galactose | nd | nd |
| | Glucose | nd | nd |
| | Mannose | nd | nd |
| | N-acetyl-neuraminic acid | 0.3512 | 100.0 |
| | N-glycol-neuraminic acid | nd | nd |
| | Total | 0.3512 | 100.0 |
| CA215 5 # 070801-5 | Fucose | nd | nd |
| | N-acetyl-galactosamine | 0.4961 | 34.2 |
| | N-acetyl-glucosamine | 0.3506 | 24.2 |
| | Galactose | 0.3539 | 24.4 |
| | Glucose | nd | nd |
| | Mannose | nd | nd |
| | N-acetyl-neuraminic acid | 0.2307 | 15.9 |
| | N-glycol-neuraminic acid | 0.0198 | 1.3 |
| | Total | 1.4511 | 100.0 | nd = not detected.

EXAMPLE 4

Location of the Carbohydrate Epitope

Using Western blot, it has been demonstrated that the RP215-specific carbohydrate-associated epitope is localized in the Fab region of cancer cell-derived Ig heavy chain of CA215. Amino acid analysis of the CDR1, CDR2 and CDR3 regions of a number of immunoglobulin heavy chains were analyzed to locate the position of the glycosylation site. These comparisons are shown in Table 12.

TABLE 12

| Cell lines of tissues | Last 6 amino acid in FR1 | SEQ ID NO: | CDR1 | SEQ ID NO: | CDR2 | SEQ ID NO: | CDR3 | SEQ ID NO: | |
|---|---|---|---|---|---|---|---|---|---|
| T47D | SRFSSR | 114 | TSGMR | 115 | PFWNGGSQKYCADSVT | 116 | GITVPBPRLCPRN | 117 | IgG |
| ZR75-1 | SGYSFT | 118 | SYWIG | 119 | IIYPGDSDTRYSPSFQG | 120 | QBIVAFS | 121 | IgM |
| ZR75-1 | SGFNFN | 122 | TYAMT | 123 | TIAADGTWTSNADFVRG | 124 | DWYDY | 125 | IgG |
| SKBR3 | SGGSVS | 126 | SGYYWS | 127 | YIYYNGSTYENPSLKS | 128 | DIKHTYGPN | 129 | IgG |
| SKBR3 | SGLSFS | 130 | SSGMN | 131 | RIGSKAASDTTSYAASVRG | 132 | QGCGGDCHIPKM | 133 | IgA |
| MDA-MB-231 | SGFTFS | 134 | SYWMD | 135 | RISPDGRTTTYADSVEG | 136 | GYLSSH | 137 | IgM |
| Lung Cancer | SGYTFG | 138 | TYWIG | 139 | IIYPGDSDTTYSPSFRG | 140 | WDVMIGFYTA | 141 | |
| Dakiki | SGFTFS | 142 | DYGMT | 143 | GITSSVLTTYYADSVKG | 144 | AQGFAPPAS | 145 | |
| IM-9 | SGFRFD | 146 | DYAMH | 147 | GISWNSDTIDYADSVKG | 148 | TKEGGVTDIDPFDI | 149 | |
| MC116 | SGYRFT | 150 | GYYMH | 151 | RINPNSGGINYAQRFQG | 152 | TREDSGSYEY | 153 | |
| Daudi | SGYSIT | 154 | SYYIH | 155 | KTDNDGRDADYAQRFQG | 156 | VRENGQKCFDY | 157 | |

A consistent O-link glycosylation site with serine or threonine was always located proximal to the junction between FR1 and CDR1, thus indicating that the RP215-specific epitope is associated with the presence of a serine or threonine residue in this location. Absence of this O-glycosylation site results in the failure of RP215 to recognize CA215.

EXAMPLE 5

In Vivo Efficacy of RP215

Although addition of RP215 monoclonal antibody to cell cultures of OC-3-VGH ovarian cancer cells had no effect on growth, these antibodies were successful in inhibiting tumor growth in vivo. Cell culture growth was also not inhibited either by human IgG or goat anti-human IgG in vitro up to a concentration of 200 μg/ml in the cell culture.

Groups of four nude mice were implanted subcutaneously with $2\times10^6$ cells in 0.2 ml per mouse at sites near the breast for a growth period of 2-3 weeks. Treatments were performed after visible apparent growth of tumors. The experimental design is shown in Table 13. The radioactive labeling of the mAb was at a specific radioactivity of 12.5 μCi/mg.

TABLE 13

| Exp. No. | Group No. | Animal (n) | Dosage |
| --- | --- | --- | --- |
| 1. | Negative Control | 4 | Medium only |
| 2. | Positive Control | 4 | Cyclophosphonamide (60 mg/Kg) |
| 3. | Antibody (High Dose) (Naked) | 4 | RP215 Mab (10 mg/Kg) |
| 4. | Antibody (Low Dose) (Naked) | 4 | RP215 Mab (2 mg/Kg) |
| 5. | $I^{131}$-labeled Antibody (High dose) | 4 | RP215 Mab (10 mg/Kg + 125 μCi) |
| 6. | $I^{131}$-labeled Antibody | 4 | RP215 Mab (6 mg/Kg + 75 μCi) |
| 7. | $I^{131}$-labeled Antibody | 4 | RP215 Mab (2 mg/Kg + 25 μCi) |

The mice were sacrificed on day 16 after treating with antibody, and the size of tumors in each mouse was determined by weight together with the body weight. These results are shown in Table 14.

TABLE 14

| Group ID | Mouse # | Body Weight | Tumor Weight | Average of Tumor Weight | Percent |
| --- | --- | --- | --- | --- | --- |
| Negative Control | 1 | 22.23 | 0.148 | 0.13075 | 100 |
| | 2 | 22.51 | 0.133 | | |
| | 3 | 23.16 | 0.104 | | |
| | 4 | 21.14 | 0.138 | | |
| Positive Control (Cyclophosphonamide 60 mg/Kg) | 1 | 21.18 | 0.098 | 0.09575 | 73.2 |
| | 2 | 21.42 | 0.096 | | |
| | 3 | 23.37 | 0.098 | | |
| | 4 | 21.18 | 0.091 | | |
| Antibody (high dose) 10 mg/Kg) | 1 | 21.43 | 0.088 | 0.0865 | 66.2 |
| | 2 | 23.05 | 0.077 | | |
| | 3 | 22.15 | 0.095 | | |
| | 4 | 23.56 | 0.086 | | |
| Antibody (low dose) 2 mg/Kg) | 1 | 21.76 | 0.103 | 0.10225 | 78.2 |
| | 2 | 20.57 | 0.122 | | |
| | 3 | 21.98 | 0.080 | | |
| | 4 | 22.64 | 0.104 | | |
| $I^{131}$-labeled Antibody (High dose 10 mg/Kg) | 1 | 20.26 | 0.034 | 0.4575 | 35 |
| | 2 | 25.71 | 0.075 | | |
| | 3 | 20.25 | 0.048 | | |
| | 4 | 22.60 | 0.026 | | |
| $I^{131}$-labeled Antibody (Mid dose 6 mg/Kg) | 1 | 20.47 | 0.068 | 0.0705 | 53.9 |
| | 2 | 22.91 | 0.076 | | |
| | 3 | 23.00 | 0.049 | | |
| | 4 | 23.05 | 0.089 | | |
| $I^{131}$-labeled Antibody (Low dose 2 mg/Kg) | 1 | 20.03 | 0.154 | 0.11675 | 89.2 |
| | 2 | 21.46 | 0.083 | | |
| | 3 | 22.12 | 0.108 | | |
| | 4 | 20.38 | 0.122 | | |

As shown, antibodies dosed at 10 mg/kg without radioactive label reduced the tumor size more significantly than the positive control which employed 60 mg/kg of cyclophosphonamide. The $I^{131}$-labeled antibody at the same dose reduced the tumor size even more.

EXAMPLE 6

Nucleotide Sequences of RP215 Variable regions

For purposes of humanizing RP215, and as a target for mutagenesis, to obtain additional antibodies with favorable properties immunoreactive with CA215, the nucleotide sequences encoding the heavy and light chain variable regions of RP215 have been determined and are shown in Table 15, along with the deduced amino acid sequences.

TABLE 15

Nucleotide and the Deduced Amino Acid Sequences of the variable regions of RP215 Monoclonal Antibody

| Region | Length (bp) | Nucleotide Sequence |
|---|---|---|
| H Chain Variable Region-Signal Peptide (SEQ ID NO: 158) 19 amino acids | 1 | atgagatggagctgtatcatcctcttcttggtagcaacagctacaggtgtcagctcc 57<br>M  R  W  S  C  I  I  L  F  L  V  A  T  A  T  G  V  S  S |
| H Chain Variable Region (SEQ ID NO: 159) 112 amino acids | 1 | caggtccaactgcagcagcctggggctgagcttgtgatgcctggg<br>Q  V  Q  L  Q  Q  P  G  A  E  L  V  M  P  G |
| | 46 | gcttcagtgaagatgtcctgcaaggcttctggctacacattcact<br>A  S  V  K  M  S  C  K  A  S  G  Y  T  F  T |
| | 91 | gactactggatgcactgggtgaagcagaggcctggacaaggcctt<br>D  Y  W  M  H  W  V  K  Q  R  P  G  Q  G  L |
| | 136 | gagtggatcggagcgattgatacttctgatagttatactaggtac<br>E  W  I  G  A  I  D  T  S  D  S  Y  T  R  Y |
| | 181 | aatcaaaagttcaaggacaaggccacattgactgtagacgaatcc<br>N  Q  K  F  K  D  K  A  T  L  T  V  D  E  S |
| | 226 | tccagcacagccttcatgcagctcagcagcctgacatctgaggac<br>S  S  T  A  F  M  Q  L  S  S  L  T  S  E  D |
| | 271 | tctgcggtctattactgtgcaagatccatctatgactggggccaa<br>S  A  V  Y  Y  C  A  R  S  I  Y  D  W  G  Q |
| | 316 | gggactctggtcactgtctctgca 339<br>G  T  L  V  T  V  S  A |
| L Chain Variable Region-Signal Peptide (SEQ ID NO: 160) 21 amino acids | 1 | atggaatcacagacccaggtcctcatgtttcttctgctctgggta<br>M  E  S  Q  T  Q  V  L  M  F  L  L  L  W  V |
| | 46 | tctggtggtgcctgtgca 63<br>S  G  G  A  C  A |
| L Chain Variable Region (SEQ ID NO: 161) 112 amino acids | 1 | gacattgtgatgacacagtctccatcctccctggctatgtcagta<br>D  I  V  M  T  Q  S  P  S  S  L  A  M  S  V |
| | 46 | ggacagaaggtcactatgagctgcaagtccagtcagagccttta<br>G  Q  K  V  T  M  S  C  K  S  S  Q  S  L  L |
| | 91 | aatagtagcaatcaaaagagctatttggcctggtaccagcagaaa<br>N  S  S  N  Q  K  S  Y  L  A  W  Y  Q  Q  K |
| | 136 | ccaggacagtctcctaaacttctggtatactttgcatccactagg<br>P  G  Q  S  P  K  L  L  V  Y  F  A  S  T  R |
| | 181 | gaatctggggtccctgatcgcttcataggcagtggatctgggaca<br>E  S  G  V  P  D  R  F  I  G  S  G  S  G  T |
| | 226 | gatttcactcttaccatcagcagtgtgcaggctgaagacctggca<br>D  F  T  L  T  I  S  S  V  Q  A  E  D  L  A |
| | 271 | gattacttctgtcagcaacattatagcactccgtccacgttcgga<br>D  Y  F  C  Q  Q  H  Y  S  T  P  S  T  F  G |
| | 316 | gggggaccaagctggaaataaaa 339<br>G  G  T  K  L  E  I  K |

Using this information, alternative forms of monoclonal antibodies immunoreactive with CA215 were designed and produced, including humanized forms thereof.

EXAMPLE 7

Humanization of RP215

Using the information set forth in Example 6, humanized forms of RP215 (hRP215) were prepared.

In addition, a chimeric RP215 mAb (chRP215) was prepared using the same human constant regions and the murine variable regions set forth above in Example 6.

RP215, HRP215, and chRP215 were obtained in purified form and compared as follows:

Each was coated separately at 5 μg/ml overnight in microwells. The microwells were treated with concentrated cell culture shed medium of OC-3-VGH cells (to supply CA215) and then with HRP-labeled RP215 as a detection antibody. The detection antibody was incubated with each well for 60 min. at 37° C. After 30 min, TMB substrate was added for 20 min. of color development and, after stopping the reaction, the intensity determined at 450 nm in an ELISA reader. In some cases, 10 μg/ml human IgG was added to the wells, but this had no evident effect on the signal intensity. The results are shown in Table 16.

TABLE 16

| Coated Antibodies | Relative Signal Intensity in Sandwich EIA No Human IgG | Relative Signal Intensity in Sandwich EIA 10 μg/ml Human IgG |
|---|---|---|
| RP215 | 100% | 100% |
| hRP215 | 20.6% | 21.4% |
| chRP215 | 14.5% | 15.4% |

As shown, hRP215 and chRP215 showed lower binding affinity, but nevertheless, were able to bind CA215 specifically and not affected by human IgG.

In additional experiments, RP215-coated microwells showed no binding to alkaline phosphatase-labeled goat anti-human IgG or to the Fab or Fc regions of this antibody. However, RP215 showed strong binding to goat anti-mouse IgG.

HRP215 showed little or no binding to goat anti-mouse IgG but strong binding to goat anti-human IgG. The results were similar for chRP215.

These results are shown in Table 17.

TABLE 17

| Detecting Antibodies Used | Antibodies coated in Wells | | | |
|---|---|---|---|---|
| | RP215 | hRP215 Relative Intensity | chRP215 Relative Intensity | hIgG Relative Intensity |
| Goat Anti-mouse IgG[a] | 100% | ~5% | ~7% | ~3% |
| Goat Anti-human IgG[a] | <0.5% | 100% | ~10% | 70% |
| Goat Anti-human IgFc | <0.5% | 150% | 45% | 100% |
| Goat Anti-human IgFab | <1% | 70% | 10% | 40% |

[a]Signal intensity for goat anti-mouse IgG and goat anti-human IgG were adjusted to 100% for comparative purposes As shown in Table 17, wells were coated with either RP215, human RP215 (hRP215), chimeric human RP215 (chRP215) or human IgG. In row 1, the results were normalized to 100% for the interaction between RP215 and goat anti-mouse IgG. As shown in the first row, goat anti-mouse IgG bound comparatively poorly to the humanized or chimeric human forms.

In row 2, when goat anti-human IgG is used as a detector, and humanized RP215 was set at 100%, decreased binding was shown for human IgG, and very reduced binding for the chimeric or murine RP215.

In row 3, when the detecting antibody was goat anti-human IgFc, strong binding was shown to the humanized RP215 and to human IgG, but reduced binding to chimeric human RP215 and virtually no binding to RP215 itself.

In row 4, when goat anti-human IgFab was used, strong binding was detected in the humanized RP215 but relatively poor binding of human IgG and very weak binding, as expected, to RP215 and chimeric RP215.

From this, it was concluded that
(1) The humanized antibody, hRP215 and chimeric antibody, chRP215 showed comparable low crossreactivity to goat anti-mouse IgG to that of human IgG.
(2) Both hRP215 and chRP215 showed similar high binding activity to goat anti-human IgFc antibodies to that of human IgG as compared to the very weak binding of RP215, which is of mouse origin. chRP215, in contrast, has very low binding activity to goat anti-human IgFab.

These results demonstrate that the humanized antibody retains antigen binding specificity to CA215 and has human characteristics to the exclusion of murine characteristics.

EXAMPLE 8

Analysis of Cancer Cell Lines for the Presence of CA215

The presence of RP215-specific epitope(s) in more than 30 cancer cell lines from ATCC and others has been tested using Western blot assay and sandwich EIA. The following cancer cell lines were shown to be positive for the presence of RP215-related epitope (>90%) in cancer cell extracts and in cell cultured shed media.

Breast Cancer Cell Lines:
MCF7 (HTB-22), MDA-MB-231 (HTB-26), MDA-MB-468 (HTB-132), MDA-435, SW-48 (CCL-231), T-47D (HTB-133)
Cervical Cancer Cell Lines:
C-33A (HTB-31), ME-180 (HTB-33)
Colon Cancer Cell Lines:
HCT 115 (ABM), HCT 116 (CCL-247), HT29 (HTB-38)
Liver Cancer Cell Lines:
Hep3B (HB-8064), HepG2 (HB-8065), Hep-2 (CCL-23)
Kidney Cancer Cell Lines:
293 (UBC)
Lung Cancer Cell Lines:
A549 (CCL-185), Calu-6 (HTB-56), H441(HTB-174), MRC-5 (CCL-171), WI-38 (CCL-75)
Lymphoma
HEL (ABM)
Melanoma
MMAN, MMRU, SK-Mel-3 (HTB-69)
Neuroblastoma
SH-SY5Y (CRL-2266), Neuro2A (CCL-131),
Bone Cancer Cell Line
U-20S (HTB-96)
Ovarian Cancer Cell Line
Skov-3 (HTB-77), OC-3-VGH (Taiwan)
Prostate Cancer Cell Line
DU 145 (HTB-81), PC-3 (CRL-1435)

However the existence of RP215-specific epitope cannot be easily demonstrated in several cancer cell lines. They are: SiHa (HTB-35, cervical), JEG-3 (HTB-36, placenta) and Jurkat (TIB-152, T-cell leukemia).

SEQUENCE LISTING

```
<160> NUMBER OF SEQ ID NOS: 161

<210> SEQ ID NO 1
<211> LENGTH: 8
<212> TYPE: PRT
<213> ORGANISM: Homo sapiens

<400> SEQUENCE: 1

Val Glu Leu Val Glu Ser Gly Ala
1               5

<210> SEQ ID NO 2
<211> LENGTH: 12
<212> TYPE: PRT
<213> ORGANISM: Homo sapiens
```

-continued

```
<220> FEATURE:
<221> NAME/KEY: PEPTIDE
<222> LOCATION: (1)...(12)
<223> OTHER INFORMATION: Tryptic peptide fragment of CA215

<400> SEQUENCE: 2

Lys Asp Val Leu Thr Ile Thr Leu Thr Pro Lys Val
1               5                   10

<210> SEQ ID NO 3
<211> LENGTH: 12
<212> TYPE: PRT
<213> ORGANISM: Homo sapiens
<220> FEATURE:
<221> NAME/KEY: PEPTIDE
<222> LOCATION: (1)...(12)
<223> OTHER INFORMATION: Tryptic peptide fragment of CA215

<400> SEQUENCE: 3

Lys Ala Pro Gln Val Tyr Thr Ile Pro Pro Lys Glu
1               5                   10

<210> SEQ ID NO 4
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: Tryptic peptide fragment of CA215

<400> SEQUENCE: 4

Arg Val Asn Ser Ala Ala Phe Pro Ala Pro Ile Glu Lys Thr
1               5                   10

<210> SEQ ID NO 5
<211> LENGTH: 17
<212> TYPE: PRT
<213> ORGANISM: Homo sapiens
<220> FEATURE:
<221> NAME/KEY: PEPTIDE
<222> LOCATION: (1)...(17)
<223> OTHER INFORMATION: Tryptic peptide fragment of CA215

<400> SEQUENCE: 5

Lys Ala Pro Gln Val Tyr Thr Ile Pro Pro Lys Glu Gln Met Ala Lys
1               5                   10                  15

Asp

<210> SEQ ID NO 6
<211> LENGTH: 18
<212> TYPE: PRT
<213> ORGANISM: Homo sapiens
<220> FEATURE:
<221> NAME/KEY: PEPTIDE
<222> LOCATION: (1)...(18)
<223> OTHER INFORMATION: Tryptic peptide fragment of CA215

<400> SEQUENCE: 6

Arg Ser Val Ser Glu Leu Pro Ile Met His Gln Asp Trp Leu Asn Gly
1               5                   10                  15

Lys Glu

<210> SEQ ID NO 7
<211> LENGTH: 19
<212> TYPE: PRT
<213> ORGANISM: Homo sapiens
<220> FEATURE:
```

```
<221> NAME/KEY: PEPTIDE
<222> LOCATION: (1)...(19)
<223> OTHER INFORMATION: Tryptic peptide fragment of CA215

<400> SEQUENCE: 7

Lys Asn Thr Gln Pro Ile Met Asp Thr Asp Gly Ser Tyr Phe Val Tyr
1               5                   10                  15

Ser Lys Leu

<210> SEQ ID NO 8
<211> LENGTH: 13
<212> TYPE: PRT
<213> ORGANISM: Homo sapiens
<220> FEATURE:
<221> NAME/KEY: PEPTIDE
<222> LOCATION: (1)...(13)
<223> OTHER INFORMATION: Tryptic peptide fragment of CA215

<400> SEQUENCE: 8

Lys Ser Ser Gly Thr Ser Tyr Pro Asp Val Leu Lys Cys
1               5                   10

<210> SEQ ID NO 9
<211> LENGTH: 11
<212> TYPE: PRT
<213> ORGANISM: Homo sapiens
<220> FEATURE:
<221> NAME/KEY: PEPTIDE
<222> LOCATION: (1)...(11)
<223> OTHER INFORMATION: Tryptic peptide fragment of CA215

<400> SEQUENCE: 9

Lys Val Cys Asn Tyr Val Ser Trp Ile Lys Gln
1               5                   10

<210> SEQ ID NO 10
<211> LENGTH: 11
<212> TYPE: PRT
<213> ORGANISM: Homo sapiens
<220> FEATURE:
<221> NAME/KEY: PEPTIDE
<222> LOCATION: (1)...(11)
<223> OTHER INFORMATION: Tryptic peptide fragment of CA215

<400> SEQUENCE: 10

Arg Thr Leu Tyr Leu Gln Met Asn Ser Leu Arg
1               5                   10

<210> SEQ ID NO 11
<211> LENGTH: 25
<212> TYPE: PRT
<213> ORGANISM: Homo sapiens
<220> FEATURE:
<221> NAME/KEY: PEPTIDE
<222> LOCATION: (1)...(25)
<223> OTHER INFORMATION: Tryptic peptide fragment of CA215

<400> SEQUENCE: 11

Ser Leu Val Val Ala Ala Val Ala Pro Asp Asn Arg Asn Pro Ala Phe
1               5                   10                  15

Thr Thr Met Gly Trp Leu Phe Leu Lys
            20                  25

<210> SEQ ID NO 12
<211> LENGTH: 9
<212> TYPE: PRT
<213> ORGANISM: Homo sapiens
<220> FEATURE:
```

-continued

```
<221> NAME/KEY: PEPTIDE
<222> LOCATION: (1)...(9)
<223> OTHER INFORMATION: Tryptic peptide fragment of CA215

<400> SEQUENCE: 12

Gly Asp Arg Val Thr Ile Thr Trp Arg
1               5

<210> SEQ ID NO 13
<211> LENGTH: 10
<212> TYPE: PRT
<213> ORGANISM: Homo sapiens
<220> FEATURE:
<221> NAME/KEY: PEPTIDE
<222> LOCATION: (1)...(10)
<223> OTHER INFORMATION: Tryptic peptide fragment of CA215

<400> SEQUENCE: 13

Gly Leu Ser Asp Ser Val Arg Ser Cys Arg
1               5                   10

<210> SEQ ID NO 14
<211> LENGTH: 19
<212> TYPE: PRT
<213> ORGANISM: Homo sapiens
<220> FEATURE:
<221> NAME/KEY: PEPTIDE
<222> LOCATION: (1)...(19)
<223> OTHER INFORMATION: Tryptic peptide fragment of CA215

<400> SEQUENCE: 14

Thr Ala Lys Gly Ser Thr Gly Met Glu Ile Leu Leu Ser Thr Leu Glu
1               5                   10                  15

Asn Thr Lys

<210> SEQ ID NO 15
<211> LENGTH: 12
<212> TYPE: PRT
<213> ORGANISM: Homo sapiens
<220> FEATURE:
<221> NAME/KEY: PEPTIDE
<222> LOCATION: (1)...(12)
<223> OTHER INFORMATION: Tryptic peptide fragment of CA215

<400> SEQUENCE: 15

Lys Val Thr Cys Val Val Val Asp Ile Ser Lys Asp
1               5                   10

<210> SEQ ID NO 16
<211> LENGTH: 14
<212> TYPE: PRT
<213> ORGANISM: Homo sapiens
<220> FEATURE:
<221> NAME/KEY: PEPTIDE
<222> LOCATION: (1)...(14)
<223> OTHER INFORMATION: Tryptic peptide fragment of CA215

<400> SEQUENCE: 16

Gly Pro Leu Cys Gly Cys Cys Pro Gly Arg Ser Ser Gln Lys
1               5                   10

<210> SEQ ID NO 17
<211> LENGTH: 10
<212> TYPE: PRT
<213> ORGANISM: Homo sapiens
<220> FEATURE:
<221> NAME/KEY: PEPTIDE
<222> LOCATION: (1)...(10)
<223> OTHER INFORMATION: Tryptic peptide fragment of CA215
```

```
<400> SEQUENCE: 17

Ala Glu Leu Gly Gly Leu Leu Ser Pro Arg
1               5                   10

<210> SEQ ID NO 18
<211> LENGTH: 21
<212> TYPE: PRT
<213> ORGANISM: Homo sapiens
<220> FEATURE:
<221> NAME/KEY: PEPTIDE
<222> LOCATION: (1)...(21)
<223> OTHER INFORMATION: Tryptic peptide fragment of CA215

<400> SEQUENCE: 18

Asp Gly Ser Ile Ser Ile Leu Gly Ser Asp Asp Ala Thr Thr Cys His
1               5                   10                  15

Ile Val Val Leu Arg
            20

<210> SEQ ID NO 19
<211> LENGTH: 11
<212> TYPE: PRT
<213> ORGANISM: Homo sapiens
<220> FEATURE:
<221> NAME/KEY: PEPTIDE
<222> LOCATION: (1)...(11)
<223> OTHER INFORMATION: Tryptic peptide fragment of CA215

<400> SEQUENCE: 19

Arg Thr Leu Tyr Leu Gln Met Asn Ser Leu Arg
1               5                   10

<210> SEQ ID NO 20
<211> LENGTH: 12
<212> TYPE: PRT
<213> ORGANISM: Homo sapiens
<220> FEATURE:
<221> NAME/KEY: PEPTIDE
<222> LOCATION: (1)...(12)
<223> OTHER INFORMATION: Tryptic peptide fragment of CA215

<400> SEQUENCE: 20

Lys Cys Glu Leu Asn Cys Gln Ala Met Gly Tyr Arg
1               5                   10

<210> SEQ ID NO 21
<211> LENGTH: 21
<212> TYPE: PRT
<213> ORGANISM: Homo sapiens
<220> FEATURE:
<221> NAME/KEY: PEPTIDE
<222> LOCATION: (1)...(21)
<223> OTHER INFORMATION: Tryptic peptide fragment of CA215

<400> SEQUENCE: 21

Leu Ser Gly Ser Cys Arg Ser Thr Asp Ser Leu His Pro Cys Pro Pro
1               5                   10                  15

Thr Ala Leu Pro Arg
            20

<210> SEQ ID NO 22
<211> LENGTH: 10
<212> TYPE: PRT
<213> ORGANISM: Homo sapiens
<220> FEATURE:
<221> NAME/KEY: PEPTIDE
<222> LOCATION: (1)...(10)
```

-continued

```
<223> OTHER INFORMATION: Tryptic peptide fragment of CA215

<400> SEQUENCE: 22

Ala Pro Thr Val Val Leu Met Met Thr Lys
1               5                   10

<210> SEQ ID NO 23
<211> LENGTH: 21
<212> TYPE: PRT
<213> ORGANISM: Homo sapiens
<220> FEATURE:
<221> NAME/KEY: PEPTIDE
<222> LOCATION: (1)...(21)
<223> OTHER INFORMATION: Tryptic peptide fragment of CA215

<400> SEQUENCE: 23

Ala Thr Ser Arg Gly Cys Ile Thr Ile Ile Gly Gly Gly Asp Thr Ala
1               5                   10                  15

Thr Cys Cys Ala Lys
            20

<210> SEQ ID NO 24
<211> LENGTH: 18
<212> TYPE: PRT
<213> ORGANISM: Homo sapiens
<220> FEATURE:
<221> NAME/KEY: PEPTIDE
<222> LOCATION: (1)...(18)
<223> OTHER INFORMATION: Tryptic peptide fragment of CA215

<400> SEQUENCE: 24

Met Ser Thr Arg Tyr His Gln Ala Ala Ser Asp Ser Tyr Leu Glu Leu
1               5                   10                  15

Ile Lys

<210> SEQ ID NO 25
<211> LENGTH: 17
<212> TYPE: PRT
<213> ORGANISM: Homo sapiens
<220> FEATURE:
<221> NAME/KEY: PEPTIDE
<222> LOCATION: (1)...(17)
<223> OTHER INFORMATION: Tryptic peptide fragment of CA215

<400> SEQUENCE: 25

Ser Leu Pro Gly Ser Pro Lys Asp Ser Ser His Leu Leu Ser Pro Leu
1               5                   10                  15

Arg

<210> SEQ ID NO 26
<211> LENGTH: 22
<212> TYPE: PRT
<213> ORGANISM: Homo sapiens
<220> FEATURE:
<221> NAME/KEY: PEPTIDE
<222> LOCATION: (1)...(22)
<223> OTHER INFORMATION: Tryptic peptide fragment of CA215

<400> SEQUENCE: 26

Gly Gly Asn Ser Gly Gly Ser Ser Ser Ile Cys Tyr Val Leu Leu Gly
1               5                   10                  15

Phe Ile Gly Thr Ser Lys
            20

<210> SEQ ID NO 27
<211> LENGTH: 16
```

```
<212> TYPE: PRT
<213> ORGANISM: Homo sapiens
<220> FEATURE:
<221> NAME/KEY: PEPTIDE
<222> LOCATION: (1)...(16)
<223> OTHER INFORMATION: Tryptic peptide fragment of CA215

<400> SEQUENCE: 27

Ala Glu Asp Thr Ala Val Tyr Tyr Cys Ala Lys Thr Leu Thr Ile Arg
1               5                   10                  15

<210> SEQ ID NO 28
<211> LENGTH: 23
<212> TYPE: PRT
<213> ORGANISM: Homo sapiens
<220> FEATURE:
<221> NAME/KEY: PEPTIDE
<222> LOCATION: (1)...(23)
<223> OTHER INFORMATION: Tryptic peptide fragment of CA215

<400> SEQUENCE: 28

Gly Leu Glu Cys Ile Gly Tyr Met Tyr Ser Ser Gly Ser Ser Phe Tyr
1               5                   10                  15

Asn Pro Ser Leu Lys Ser Arg
            20

<210> SEQ ID NO 29
<211> LENGTH: 15
<212> TYPE: PRT
<213> ORGANISM: Homo sapiens
<220> FEATURE:
<221> NAME/KEY: PEPTIDE
<222> LOCATION: (1)...(15)
<223> OTHER INFORMATION: Tryptic peptide fragment of CA215

<400> SEQUENCE: 29

Met Ala Tyr Leu Gln Gln Thr Leu Ala Gly Pro Ser Gly Thr Arg
1               5                   10                  15

<210> SEQ ID NO 30
<211> LENGTH: 25
<212> TYPE: PRT
<213> ORGANISM: Homo sapiens

<400> SEQUENCE: 30

Lys Gly His Gln Asp Ser Cys Pro Phe Glu Leu Thr Ala Cys Pro Asn
1               5                   10                  15

Glu Gly Cys Thr Ser Gln Val Pro Arg
            20                  25

<210> SEQ ID NO 31
<211> LENGTH: 22
<212> TYPE: PRT
<213> ORGANISM: Homo sapiens
<220> FEATURE:
<221> NAME/KEY: PEPTIDE
<222> LOCATION: (1)...(22)
<223> OTHER INFORMATION: Tryptic peptide fragment of CA215

<400> SEQUENCE: 31

Gly Leu Glu Trp Val Ser Ala Val Ser Gly Ser Gly Thr Thr Thr Tyr
1               5                   10                  15

Tyr Ala Asp Ser Val Lys
            20

<210> SEQ ID NO 32
<211> LENGTH: 16
```

-continued

```
<212> TYPE: PRT
<213> ORGANISM: Homo sapiens
<220> FEATURE:
<221> NAME/KEY: PEPTIDE
<222> LOCATION: (1)...(16)
<223> OTHER INFORMATION: Tryptic peptide fragment of CA215

<400> SEQUENCE: 32

Leu Ser Ser Val Thr Ala Ala Asp Thr Asn Val Tyr Tyr Cys Ala Arg
1               5                   10                  15

<210> SEQ ID NO 33
<211> LENGTH: 15
<212> TYPE: PRT
<213> ORGANISM: Homo sapiens
<220> FEATURE:
<221> NAME/KEY: PEPTIDE
<222> LOCATION: (1)...(15)
<223> OTHER INFORMATION: Tryptic peptide fragment of CA215

<400> SEQUENCE: 33

Ala Glu Thr Leu Val Phe Ser Thr His Ala Val Ile Ser Met Arg
1               5                   10                  15

<210> SEQ ID NO 34
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR1 region of T47D(IgG) heavy chain

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Arg Phe Ser Ser Arg
            20                  25                  30

<210> SEQ ID NO 35
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of T47D(IgG) heavy chain

<400> SEQUENCE: 35

Thr Ser Gly Met Arg
1               5

<210> SEQ ID NO 36
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR1 region of ZR75-1 (IgM) heavy chain

<400> SEQUENCE: 36

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30

<210> SEQ ID NO 37
```

```
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of ZR75-1 (IgM) heavy chain

<400> SEQUENCE: 37

Ser Tyr Trp Ile Gly
1               5

<210> SEQ ID NO 38
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR1 region of ZR75-1 (IgG) heavy chain

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Asn Phe Asn
            20                  25                  30

<210> SEQ ID NO 39
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of ZR75-1 (IgG) heavy chain

<400> SEQUENCE: 39

Thr Tyr Ala Met Thr
1               5

<210> SEQ ID NO 40
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR1 region of SKBR3 (IgG) heavy chain

<400> SEQUENCE: 40

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser
            20                  25                  30

<210> SEQ ID NO 41
<211> LENGTH: 7
<212> TYPE: PRT
<213> ORGANISM: Homo sapiens
<220> FEATURE:
<221> NAME/KEY: DOMAIN
<222> LOCATION: (1)...(7)
<223> OTHER INFORMATION: CDR1 region of SKBR3 (IgG) heavy chain

<400> SEQUENCE: 41

Ser Gly Tyr Tyr Tyr Trp Ser
1               5
```

```
<210> SEQ ID NO 42
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR1 region of SKBR3 (IgA) heavy chain

<400> SEQUENCE: 42

Glu Val Gln Leu Val Glu Ser Gly Gly Gly Leu Val Gln Pro Gly Gly
1               5                   10                  15

Ser Leu Thr Leu Ser Cys Ala Val Ser Gly Leu Ser Phe Ser
            20                  25                  30

<210> SEQ ID NO 43
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of SKBR3 (IgA) heavy chain

<400> SEQUENCE: 43

Ser Ser Gly Met Asn
1               5

<210> SEQ ID NO 44
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR1 region of MDA-MB-231 (IgM) heavy chain

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 45
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of MDA-MB-231 (IgM) heavy chain

<400> SEQUENCE: 45

Ser Tyr Trp Met Asp
1               5

<210> SEQ ID NO 46
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR1 region of Lung Cancer heavy chain

<400> SEQUENCE: 46

Glu Val Gln Leu Glu Glu Ser Gly Ala Glu Val Lys Lys Pro Gly Glu
1               5                   10                  15
```

Ser Leu Lys Ile Ser Cys Glu Ala Ser Gly Tyr Thr Phe Gly
            20                  25                  30

<210> SEQ ID NO 47
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of Lung Cancer heavy chain

<400> SEQUENCE: 47

Thr Tyr Trp Ile Gly
1               5

<210> SEQ ID NO 48
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: FR1 region of CA215

<400> SEQUENCE: 48

Lys Ser Ser Gly Thr Ser Tyr Pro Asp Val Leu Lys Cys Lys Val Cys
1               5                  10                  15

Asn

<210> SEQ ID NO 49
<211> LENGTH: 4
<212> TYPE: PRT
<213> ORGANISM: Homo sapiens
<220> FEATURE:
<221> NAME/KEY: DOMAIN
<222> LOCATION: (1)...(4)
<223> OTHER INFORMATION: CDR1 region of CA215

<400> SEQUENCE: 49

Tyr Val Ser Trp
1

<210> SEQ ID NO 50
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: Alternate FR1 comparison region of CA215

<400> SEQUENCE: 50

Ser Leu Val Val Ala Ala Val Ala Pro Asp Asn Arg Asn Pro Ala Phe
1               5                  10                  15

Thr

<210> SEQ ID NO 51
<211> LENGTH: 21
<212> TYPE: PRT
<213> ORGANISM: Homo sapiens
<220> FEATURE:
<221> NAME/KEY: DOMAIN
<222> LOCATION: (1)...(21)
<223> OTHER INFORMATION: Alternate FR1 comparison region of CA215

<400> SEQUENCE: 51

Ala Thr Ser Arg Gly Cys Ile Thr Ile Ile Gly Gly Gly Asp Thr Ala

```
1               5                   10                  15

Thr Cys Cys Ala Lys
            20

<210> SEQ ID NO 52
<211> LENGTH: 15
<212> TYPE: PRT
<213> ORGANISM: Homo sapiens
<220> FEATURE:
<221> NAME/KEY: DOMAIN
<222> LOCATION: (1)...(15)
<223> OTHER INFORMATION: Alternate FR1 comparison region of CA215

<400> SEQUENCE: 52

Met Ala Tyr Leu Gln Gln Thr Leu Ala Gly Pro Ser Gly Thr Arg
1               5                   10                  15

<210> SEQ ID NO 53
<211> LENGTH: 13
<212> TYPE: PRT
<213> ORGANISM: Homo sapiens
<220> FEATURE:
<221> NAME/KEY: DOMAIN
<222> LOCATION: (1)...(13)
<223> OTHER INFORMATION: FR2 region of T47D (IgG) heavy chain

<400> SEQUENCE: 53

Trp Val Arg Gln Ala Pro Gly Lys Glu Leu Glu Val Ala
1               5                   10

<210> SEQ ID NO 54
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: CDR2 region of T47D(IgG) heavy chain

<400> SEQUENCE: 54

Pro Phe Trp Asn Gly Gly Ser Gln Lys Tyr Cys Ala Asp Ser Val Thr
1               5                   10                  15

<210> SEQ ID NO 55
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: FR2 region of ZR75-1(IgM) heavy chain

<400> SEQUENCE: 55

Trp Val Arg Gln Met Pro Gly Lys Gly Leu Glu Trp Met Gly
1               5                   10

<210> SEQ ID NO 56
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of ZR75-1(IgM) heavy chain

<400> SEQUENCE: 56

Ile Ile Tyr Pro Gly Asp Ser Asp Thr Arg Tyr Ser Pro Ser Phe Gln
1               5                   10                  15
```

Gly

```
<210> SEQ ID NO 57
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: FR2 region of ZR75-1 (IgG) heavy chain

<400> SEQUENCE: 57
```

Trp Val Arg Gln Ala Pro Gly Lys Gly Leu Glu Trp Val Ser
1               5                   10

```
<210> SEQ ID NO 58
<211> LENGTH: 17
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: CDR2 region of ZR75-1 (IgG) heavy chain

<400> SEQUENCE: 58
```

Thr Ile Ala Ala Asp Gly Thr Trp Thr Ser Asn Ala Asp Phe Val Arg
1               5                   10                  15

Gly

```
<210> SEQ ID NO 59
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: FR2 region of SKBR3 (IgG) heavy chain

<400> SEQUENCE: 59
```

Arg Ile Arg Gln His Pro Gly Lys Gly Leu Glu Trp Ile Gly
1               5                   10

```
<210> SEQ ID NO 60
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: CDR2 region of SKBR3 (IgG) heavy chain

<400> SEQUENCE: 60
```

Tyr Ile Tyr Tyr Asn Gly Ser Thr Tyr Glu Asn Pro Ser Leu Lys Ser
1               5                   10                  15

```
<210> SEQ ID NO 61
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: FR2 region of SKBR3 (IgA) heavy chain

<400> SEQUENCE: 61
```

Trp Val Arg Gln Ala Ser Gly Lys Gly Leu Glu Trp Val Gly
1               5                   10

```
<210> SEQ ID NO 62
<211> LENGTH: 19
<212> TYPE: PRT
<213> ORGANISM: Homo sapiens
<220> FEATURE:
<221> NAME/KEY: DOMAIN
<222> LOCATION: (1)...(19)
<223> OTHER INFORMATION: CDR2 region of SKBR3 (IgA) heavy chain

<400> SEQUENCE: 62

Arg Ile Gly Ser Lys Ala Ala Ser Asp Thr Thr Ser Tyr Ala Ala Ser
1               5                   10                  15

Val Arg Gly

<210> SEQ ID NO 63
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: FR2 region of MDA-MB-231 (IgM) heavy chain

<400> SEQUENCE: 63

Trp Val Arg Gln Val Pro Gly Lys Gly Leu Val Trp Val Ser
1               5                   10

<210> SEQ ID NO 64
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of MDA-MB-231 (IgM) heavy chain

<400> SEQUENCE: 64

Arg Ile Ser Pro Asp Gly Arg Thr Thr Thr Tyr Ala Asp Ser Val Glu
1               5                   10                  15

Gly

<210> SEQ ID NO 65
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: FR2 region of Lung Cancer heavy chain

<400> SEQUENCE: 65

Trp Val Arg Gln Met Pro Gly Lys Gly Leu Glu Trp Met Gly
1               5                   10

<210> SEQ ID NO 66
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: FR2 region of Lung Cancer heavy chain

<400> SEQUENCE: 66

Ile Ile Tyr Pro Gly Asp Ser Asp Thr Thr Tyr Ser Pro Ser Phe Arg
1               5                   10                  15

Gly
```

```
<210> SEQ ID NO 67
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: FR2 region of CA215

<400> SEQUENCE: 67

Ile Lys Gln Gly Leu Glu Trp Val Ser
1               5

<210> SEQ ID NO 68
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: CDR2 region of CA215

<400> SEQUENCE: 68

Ala Val Ser Gly Ser Gly Thr Thr Thr Tyr Tyr Ala Asp Ser Val Lys
1               5                   10                  15

<210> SEQ ID NO 69
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: Alternate FR2 comparison region of CA215

<400> SEQUENCE: 69

Trp Leu Phe Leu Lys
1               5

<210> SEQ ID NO 70
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Alternate FR2 comparison region of CA215

<400> SEQUENCE: 70

Gly Leu Glu Cys Ile Gly
1               5

<210> SEQ ID NO 71
<211> LENGTH: 18
<212> TYPE: PRT
<213> ORGANISM: Homo sapiens
<220> FEATURE:
<221> NAME/KEY: DOMAIN
<222> LOCATION: (1)...(18)
<223> OTHER INFORMATION: Alternate CDR2 comparison region of CA215

<400> SEQUENCE: 71

Tyr Met Tyr Ser Ser Gly Ser Ser Phe Tyr Asn Pro Ser Leu Lys Ser
1               5                   10                  15

Arg Gly

<210> SEQ ID NO 72
<211> LENGTH: 31
```

```
<212> TYPE: PRT
<213> ORGANISM: Homo sapiens
<220> FEATURE:
<221> NAME/KEY: DOMAIN
<222> LOCATION: (1)...(31)
<223> OTHER INFORMATION: FR3 region of T47D (IgG) heavy chain

<400> SEQUENCE: 72

Gly Arg Phe Thr Phe Ser Glu Thr Phe Leu Arg Pro Cys Ser Leu Cys
1               5                   10                  15

Lys Cys Thr Val Asn Leu Arg Ala Arg Pro Ser Ile Pro Ala Pro
            20                  25                  30

<210> SEQ ID NO 73
<211> LENGTH: 13
<212> TYPE: PRT
<213> ORGANISM: Homo sapiens
<220> FEATURE:
<221> NAME/KEY: DOMAIN
<222> LOCATION: (1)...(13)
<223> OTHER INFORMATION: CDR3 region of T47D (IgG) heavy chain

<400> SEQUENCE: 73

Gly Ile Thr Val Pro His Pro Arg Leu Cys Pro Arg Asn
1               5                   10

<210> SEQ ID NO 74
<211> LENGTH: 32
<212> TYPE: PRT
<213> ORGANISM: Homo sapiens
<220> FEATURE:
<221> NAME/KEY: DOMAIN
<222> LOCATION: (1)...(32)
<223> OTHER INFORMATION: FR3 region of ZR75-1 (IgM) heavy chain

<400> SEQUENCE: 74

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 75
<211> LENGTH: 7
<212> TYPE: PRT
<213> ORGANISM: Homo sapiens
<220> FEATURE:
<221> NAME/KEY: DOMAIN
<222> LOCATION: (1)...(7)
<223> OTHER INFORMATION: CDR3 region of ZR75-1 (IgM) heavy chain

<400> SEQUENCE: 75

Gln Glu Ile Val Ala Phe Ser
1               5

<210> SEQ ID NO 76
<211> LENGTH: 32
<212> TYPE: PRT
<213> ORGANISM: Homo sapiens
<220> FEATURE:
<221> NAME/KEY: DOMAIN
<222> LOCATION: (1)...(32)
<223> OTHER INFORMATION: FR3 region of ZR75-1 (IgG) heavy chain

<400> SEQUENCE: 76

Arg Leu Thr Ile Ser Arg Asp Asn Ser Arg Asn Thr Leu Tyr Leu Gln
1               5                   10                  15

Met Asn Ser Leu Arg Ala Glu Asp Thr Ala Ile Tyr Phe Cys Ala Lys
            20                  25                  30
```

```
<210> SEQ ID NO 77
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR3 region of ZR75-1 (IgG) heavy chain

<400> SEQUENCE: 77

Asp Trp Tyr Asp Tyr
1               5

<210> SEQ ID NO 78
<211> LENGTH: 32
<212> TYPE: PRT
<213> ORGANISM: Homo sapiens
<220> FEATURE:
<221> NAME/KEY: DOMAIN
<222> LOCATION: (1)...(32)
<223> OTHER INFORMATION: FR3 region of SKBR3 (IgG) heavy chain

<400> SEQUENCE: 78

Arg Ala Ser Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 79
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: CDR3 region of SKBR3 (IgG) heavy chain

<400> SEQUENCE: 79

Asp Ile Lys His Thr Tyr Gly Pro Asn
1               5

<210> SEQ ID NO 80
<211> LENGTH: 32
<212> TYPE: PRT
<213> ORGANISM: Homo sapiens
<220> FEATURE:
<221> NAME/KEY: DOMAIN
<222> LOCATION: (1)...(32)
<223> OTHER INFORMATION: FR3 region of SKBR3 (IgA) heavy chain

<400> SEQUENCE: 80

Arg Phe Phe Ile Ser Arg Asp Asp Ser Lys Lys Thr Val Tyr Leu Gln
1               5                   10                  15

Met Asn Ser Leu Lys Thr Glu Asp Thr Ala Val Tyr Tyr Cys Ser Arg
            20                  25                  30

<210> SEQ ID NO 81
<211> LENGTH: 12
<212> TYPE: PRT
<213> ORGANISM: Homo sapiens
<220> FEATURE:
<221> NAME/KEY: DOMAIN
<222> LOCATION: (1)...(12)
<223> OTHER INFORMATION: CDR3 region of SKBR3 (IgA) heavy chain

<400> SEQUENCE: 81

Gln Gly Cys Gly Gly Asp Cys His Ile Pro Lys Met
```

```
1               5                    10
```

<210> SEQ ID NO 82
<211> LENGTH: 32
<212> TYPE: PRT
<213> ORGANISM: Homo sapiens
<220> FEATURE:
<221> NAME/KEY: DOMAIN
<222> LOCATION: (1)...(32)
<223> OTHER INFORMATION: FR3 region of MDA-MB-231 (IgM) heavy chain

<400> SEQUENCE: 82

```
Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Gly
            20                  25                  30
```

<210> SEQ ID NO 83
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: CDR3 region of MDA-MB-231 (IgM) heavy chain

<400> SEQUENCE: 83

```
Gly Tyr Leu Ser Ser His
1               5
```

<210> SEQ ID NO 84
<211> LENGTH: 32
<212> TYPE: PRT
<213> ORGANISM: Homo sapiens
<220> FEATURE:
<221> NAME/KEY: DOMAIN
<222> LOCATION: (1)...(32)
<223> OTHER INFORMATION: FR3 region of Lung Cancer heavy chain

<400> SEQUENCE: 84

```
Gln Val Thr Leu Ser Val Asp Lys Phe Ile Asn Thr Ala Tyr Leu Gln
1               5                   10                  15

Trp Asp Ser Leu Lys Ala Ser Asp Thr Ala Ile Tyr Tyr Cys Ala Arg
            20                  25                  30
```

<210> SEQ ID NO 85
<211> LENGTH: 10
<212> TYPE: PRT
<213> ORGANISM: Homo sapiens
<220> FEATURE:
<221> NAME/KEY: DOMAIN
<222> LOCATION: (1)...(10)
<223> OTHER INFORMATION: CDR3 region of Lung Cancer heavy chain

<400> SEQUENCE: 85

```
Trp Asp Val Met Ile Gly Phe Tyr Thr Ala
1               5                   10
```

<210> SEQ ID NO 86
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: FR3 region of CA215

<400> SEQUENCE: 86

Asp Arg Val Thr Ile Thr Trp Arg Arg Thr Leu Tyr Leu Gln Met Asn
1               5                   10                  15

Ser Leu Arg Ala Glu Asp Thr Ala Val Tyr Tyr Cys Ala Lys
            20                  25                  30

<210> SEQ ID NO 87
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR3 region of CA215

<400> SEQUENCE: 87

Thr Leu Thr Ile Arg
1               5

<210> SEQ ID NO 88
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: Alternate FR3 comparison region of CA215

<400> SEQUENCE: 88

Leu Ser Ser Val Thr Ala Ala Asp Thr Asn Val Tyr Tyr Cys Ala Arg
1               5                   10                  15

<210> SEQ ID NO 89
<211> LENGTH: 15
<212> TYPE: PRT
<213> ORGANISM: Homo sapiens
<220> FEATURE:
<221> NAME/KEY: DOMAIN
<222> LOCATION: (1)...(15)
<223> OTHER INFORMATION: Alternate FR3 comparison region of CA215

<400> SEQUENCE: 89

Met Ala Tyr Leu Gln Gln Thr Leu Ala Gly Pro Ser Gly Thr Arg
1               5                   10                  15

<210> SEQ ID NO 90
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: JH region of T47D (IgG) heavy chain

<400> SEQUENCE: 90

Tyr Phe Asp Ser Gly Gln Gly Thr Leu Val Thr Val Ser Ser
1               5                   10

<210> SEQ ID NO 91
<211> LENGTH: 11
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: CH region of T47D (IgG) heavy chain

<400> SEQUENCE: 91

Ala Ser Thr Lys Gly Pro Ser Val Phe Pro Leu
1               5                   10

<210> SEQ ID NO 92
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: JH region of ZR75-1 (IgM) heavy chain

<400> SEQUENCE: 92

Tyr Tyr Tyr Met Asp Val Trp Gly Lys Gly Thr Thr Val Thr Val Ser
1               5                   10                  15

Ser

<210> SEQ ID NO 93
<211> LENGTH: 11
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: CH region of ZR75-1 (IgM) heavy chain

<400> SEQUENCE: 93

Gly Ser Ala Ser Pro Gln Pro Phe Ser Pro Ser
1               5                   10

<210> SEQ ID NO 94
<211> LENGTH: 11
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: JH region of ZR75-1 (IgG) heavy chain

<400> SEQUENCE: 94

Trp Gly Gln Gly Thr Leu Val Thr Ala Leu Leu
1               5                   10

<210> SEQ ID NO 95
<211> LENGTH: 15
<212> TYPE: PRT
<213> ORGANISM: Homo sapiens
<220> FEATURE:
<221> NAME/KEY: DOMAIN
<222> LOCATION: (1)...(15)
<223> OTHER INFORMATION: CH region of ZR75-1 (IgG) heavy chain

<400> SEQUENCE: 95

Thr Val Ser Thr Gly Leu His Gln Gly Pro Ile Gly Leu Pro Pro
1               5                   10                  15

<210> SEQ ID NO 96
<211> LENGTH: 18
<212> TYPE: PRT
<213> ORGANISM: Homo sapiens
<220> FEATURE:
<221> NAME/KEY: DOMAIN
<222> LOCATION: (1)...(18)
<223> OTHER INFORMATION: JH region of SKBR3 (IgG) heavy chain

<400> SEQUENCE: 96

Tyr Asn Cys Tyr Met Asp Val Trp Gly Lys Gly Thr Thr Val Thr Val
1               5                   10                  15

Ser Ser

<210> SEQ ID NO 97
<211> LENGTH: 11
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: CH region of SKBR3 (IgG) heavy chain

<400> SEQUENCE: 97

Gly Leu His Gln Gly Pro Ile Gly Leu Pro Pro
1               5                   10

<210> SEQ ID NO 98
<211> LENGTH: 19
<212> TYPE: PRT
<213> ORGANISM: Homo sapiens
<220> FEATURE:
<221> NAME/KEY: DOMAIN
<222> LOCATION: (1)...(19)
<223> OTHER INFORMATION: JH region of SKBR3 (IgA) heavy chain

<400> SEQUENCE: 98

Tyr Tyr Tyr Tyr Gly Met Asp Val Trp Gly Gln Gly Thr Thr Val Thr
1               5                   10                  15

Val Ser Ser

<210> SEQ ID NO 99
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: CH region of SKBR3 (IgA) heavy chain

<400> SEQUENCE: 99

Ala Ser Pro Thr Ser Pro Lys Val Phe
1               5

<210> SEQ ID NO 100
<211> LENGTH: 13
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: JH region of MDA-MB-231 (IgM) heavy chain

<400> SEQUENCE: 100

Asp Tyr Trp Gly Arg Gly Thr Leu Val Thr Val Ser Ser
1               5                   10

<210> SEQ ID NO 101
<211> LENGTH: 11
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: CH region of MDA-MB-231 (IgM) heavy chain

<400> SEQUENCE: 101

Gly Glu Cys Ile Arg Pro Asn Pro Phe Pro Pro
1               5                   10

<210> SEQ ID NO 102
<211> LENGTH: 12

```
<212> TYPE: PRT
<213> ORGANISM: Homo sapiens
<220> FEATURE:
<221> NAME/KEY: DOMAIN
<222> LOCATION: (1)...(12)
<223> OTHER INFORMATION: JH region of Lung Cancer heavy chain

<400> SEQUENCE: 102

Asp Tyr Trp Gly Gln Gly Thr Gln Val Thr Val Ser
1               5                   10

<210> SEQ ID NO 103
<211> LENGTH: 30
<212> TYPE: PRT
<213> ORGANISM: Homo sapiens
<220> FEATURE:
<221> NAME/KEY: DOMAIN
<222> LOCATION: (1)...(30)
<223> OTHER INFORMATION: CH region of Lung Cancer heavy chain

<400> SEQUENCE: 103

Ser Ala Ser Thr Lys Gly Pro Ser Val Phe Pro Leu Ala Pro Ser Ser
1               5                   10                  15
Lys Ser Thr Ser Gly Gly Thr Ala Val Leu Gly Cys Leu Val
            20                  25                  30

<210> SEQ ID NO 104
<211> LENGTH: 10
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: CH region of Lung Cancer heavy chain

<400> SEQUENCE: 104

Lys Asp Tyr Phe Pro Glu Pro Val Thr Val
1               5                   10

<210> SEQ ID NO 105
<211> LENGTH: 19
<212> TYPE: PRT
<213> ORGANISM: Homo sapiens
<220> FEATURE:
<221> NAME/KEY: DOMAIN
<222> LOCATION: (1)...(19)
<223> OTHER INFORMATION: CH region of CA215

<400> SEQUENCE: 105

Thr Ala Lys Gly Ser Thr Gly Met Glu Ile Leu Leu Ser Thr Leu Glu
1               5                   10                  15
Asn Thr Lys

<210> SEQ ID NO 106
<211> LENGTH: 167
<212> TYPE: PRT
<213> ORGANISM: Homo sapiens
<220> FEATURE:
<221> NAME/KEY: DOMAIN
<222> LOCATION: (1)...(166)
<223> OTHER INFORMATION: Constant region of CA215

<400> SEQUENCE: 106

Gly Asn Ser Gly Gly Ser Ser Ile Cys Tyr Val Leu Leu Gly Phe
1               5                   10                  15
Ile Gly Thr Ser Lys Leu Ser Gly Ser Cys Arg Ser Thr Asp Ser Leu
            20                  25                  30
```

-continued

```
His Pro Cys Pro Pro Thr Ala Leu Pro Arg Ala Glu Leu Gly Gly Leu
        35                  40                  45

Leu Ser Pro Arg Lys Asp Val Leu Thr Ile Thr Leu Thr Pro Lys Val
    50                  55                  60

Thr Cys Val Val Val Asp Ile Ser Lys Asp Arg Ser Val Ser Glu Leu
65                  70                  75                  80

Pro Ile Met His Gln Asp Trp Leu Asn Gly Lys Glu Arg Val Asn Ser
                85                  90                  95

Ala Ala Phe Pro Ala Pro Ile Glu Lys Thr Lys Ala Pro Gln Val Tyr
            100                 105                 110

Thr Ile Pro Pro Lys Glu Gln Met Ala Lys Asp Lys Gly His Gln Asp
        115                 120                 125

Ser Cys Pro Phe Glu Leu Thr Ala Cys Pro Asn Glu Gly Cys Thr Ser
    130                 135                 140

Gln Val Pro Arg Lys Asn Thr Gln Pro Ile Met Asp Thr Asp Gly Ser
145                 150                 155                 160

Tyr Phe Val Tyr Ser Lys Leu
                165

<210> SEQ ID NO 107
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: Partial amino acid sequence of CA215

<400> SEQUENCE: 107

Gly Pro Leu Cys Gly Cys Cys Pro Gly Arg Ser Ser Gln Lys
1               5                   10

<210> SEQ ID NO 108
<211> LENGTH: 10
<212> TYPE: PRT
<213> ORGANISM: Homo sapiens
<220> FEATURE:
<221> NAME/KEY: DOMAIN
<222> LOCATION: (1)...(10)
<223> OTHER INFORMATION: Partial amino acid sequence of CA215

<400> SEQUENCE: 108

Ala Pro Thr Val Val Leu Met Met Thr Lys
1               5                   10

<210> SEQ ID NO 109
<211> LENGTH: 18
<212> TYPE: PRT
<213> ORGANISM: Homo sapiens
<220> FEATURE:
<221> NAME/KEY: DOMAIN
<222> LOCATION: (1)...(18)
<223> OTHER INFORMATION: Partial amino acid sequence of CA215

<400> SEQUENCE: 109

Met Ser Thr Arg Tyr His Gln Ala Ala Ser Asp Ser Tyr Leu Glu Leu
1               5                   10                  15

Ile Lys

<210> SEQ ID NO 110
<211> LENGTH: 17
<212> TYPE: PRT
<213> ORGANISM: Homo sapiens
<220> FEATURE:
```

```
<221> NAME/KEY: DOMAIN
<222> LOCATION: (1)...(17)
<223> OTHER INFORMATION: Partial amino acid sequence of CA215

<400> SEQUENCE: 110

Ser Leu Pro Gly Ser Pro Lys Asp Ser Ser His Leu Leu Ser Pro Leu
1               5                   10                  15

Arg

<210> SEQ ID NO 111
<211> LENGTH: 164
<212> TYPE: PRT
<213> ORGANISM: Homo sapiens
<220> FEATURE:
<221> NAME/KEY: DOMAIN
<222> LOCATION: (1)...(164)
<223> OTHER INFORMATION: Anti-human colon carcinoma heavy chain

<400> SEQUENCE: 111

Pro Lys Asp Val Leu Thr Ile Thr Leu Thr Pro Lys Val Thr Cys Val
1               5                   10                  15

Val Val Asp Ile Ser Lys Asp Asp Pro Glu Val Gln Phe Ser Trp Phe
                20                  25                  30

Val Asp Asp Val Glu Val His Thr Ala Gln Thr Gln Pro Arg Glu Glu
            35                  40                  45

Gln Phe Asn Ser Thr Phe Arg Ser Val Ser Glu Leu Pro Ile Met His
    50                  55                  60

Gln Asp Trp Leu Asn Gly Lys Glu Phe Lys Cys Arg Val Asn Ser Ala
65                  70                  75                  80

Ala Phe Pro Ala Pro Ile Glu Lys Thr Ile Ser Lys Thr Lys Gly Arg
                85                  90                  95

Pro Lys Ala Pro Gln Val Tyr Thr Ile Pro Pro Lys Glu Gln Met
            100                 105                 110

Ala Lys Asp Lys Val Ser Leu Thr Cys Met Ile Thr Asp Phe Phe Pro
            115                 120                 125

Glu Asp Ile Thr Val Glu Trp Gln Trp Asn Gly Gln Pro Ala Glu Asn
    130                 135                 140

Tyr Lys Asn Thr Gln Pro Ile Met Asp Thr Asp Gly Ser Tyr Phe Val
145                 150                 155                 160

Tyr Ser Lys Leu

<210> SEQ ID NO 112
<211> LENGTH: 110
<212> TYPE: PRT
<213> ORGANISM: Homo sapiens
<220> FEATURE:
<221> NAME/KEY: DOMAIN
<222> LOCATION: (1)...(110)
<223> OTHER INFORMATION: Constant region CA215 amino acid sequence by
      MALDI-TOF MS

<400> SEQUENCE: 112

Lys Asp Val Leu Thr Ile Thr Leu Thr Pro Lys Val Thr Cys Val Val
1               5                   10                  15

Val Asp Ile Ser Lys Asp Leu Ser Thr Leu Glu Asn Thr Lys Arg Ser
                20                  25                  30

Val Ser Glu Leu Pro Ile Met His Gln Asp Trp Leu Asn Gly Lys Glu
            35                  40                  45

Arg Val Asn Ser Ala Ala Phe Pro Ala Pro Ile Glu Lys Thr Lys Ala
    50                  55                  60
```

```
Pro Gln Val Tyr Thr Ile Pro Pro Lys Glu Gln Met Ala Lys Asp Lys
 65                  70                  75                  80

Val Thr Cys Val Val Val Asp Ile Ser Lys Asp Lys Asn Thr Gln Pro
                 85                  90                  95

Ile Met Asp Thr Asp Gly Ser Tyr Phe Val Tyr Ser Lys Leu
            100                 105                 110
```

<210> SEQ ID NO 113
<211> LENGTH: 145
<212> TYPE: PRT
<213> ORGANISM: Homo sapiens
<220> FEATURE:
<221> NAME/KEY: DOMAIN
<222> LOCATION: (1)...(145)
<223> OTHER INFORMATION: Constant region CA215 amino acid sequence by
      RT-PCR

<400> SEQUENCE: 113

```
Val Glu Val His Asn Ala Lys Thr Lys Pro Arg Glu Glu Gln Phe Asn
  1               5                  10                  15

Ser Thr Tyr Arg Val Val Ser Val Leu Thr Val Val His Gln Asp Trp
                 20                  25                  30

Leu Asn Gly Lys Glu Tyr Lys Cys Lys Val Ser Asn Lys Gly Leu Pro
             35                  40                  45

Ala Pro Ile Glu Lys Thr Ile Ser Lys Thr Lys Gly Gly Thr Arg Gly
         50                  55                  60

Cys Gly His Met Asp Arg Gly Gln Leu Gly Pro Pro Ser Ala Leu
 65                  70                  75                  80

Gly Val Thr Ala Val Pro Thr Ser Val Pro Thr Gly Gln Pro Arg Glu
                 85                  90                  95

Pro Gln Val Tyr Thr Leu Pro Pro Ser Arg Glu Glu Met Thr Lys Asn
            100                 105                 110

Gln Val Ser Leu Thr Cys Leu Val Lys Gly Phe Tyr Pro Ser Asp Ile
        115                 120                 125

Ala Val Glu Trp Glu Ser Asn Gly Gln Pro Glu Asn Asn Tyr Lys Thr
    130                 135                 140

Thr
145
```

<210> SEQ ID NO 114
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of T47D (IgG)
      heavy chain

<400> SEQUENCE: 114

```
Ser Arg Phe Ser Ser Arg
  1               5
```

<210> SEQ ID NO 115
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of T47D (IgG) heavy chain

<400> SEQUENCE: 115

```
Thr Ser Gly Met Arg
1               5

<210> SEQ ID NO 116
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: CDR2 region of T47D (IgG) heavy chain

<400> SEQUENCE: 116

Pro Phe Trp Asn Gly Gly Ser Gln Lys Tyr Cys Ala Asp Ser Val Thr
1               5                   10                  15

<210> SEQ ID NO 117
<211> LENGTH: 13
<212> TYPE: PRT
<213> ORGANISM: Homo sapiens
<220> FEATURE:
<221> NAME/KEY: DOMAIN
<222> LOCATION: (1)...(13)
<223> OTHER INFORMATION: CDR3 region of T47D (IgG) heavy chain

<400> SEQUENCE: 117

Gly Ile Thr Val Pro Asx Pro Arg Leu Cys Pro Arg Asn
1               5                   10

<210> SEQ ID NO 118
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of ZR75-1
      (IgM) heavy chain

<400> SEQUENCE: 118

Ser Gly Tyr Ser Phe Thr
1               5

<210> SEQ ID NO 119
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of ZR75-1 (IgM) heavy chain

<400> SEQUENCE: 119

Ser Tyr Trp Ile Gly
1               5

<210> SEQ ID NO 120
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of ZR75-1 (IgM) heavy chain

<400> SEQUENCE: 120

Ile Ile Tyr Pro Gly Asp Ser Asp Thr Arg Tyr Ser Pro Ser Phe Gln
1               5                   10                  15

Gly
```

```
<210> SEQ ID NO 121
<211> LENGTH: 7
<212> TYPE: PRT
<213> ORGANISM: Homo sapiens
<220> FEATURE:
<221> NAME/KEY: DOMAIN
<222> LOCATION: (1)...(7)
<223> OTHER INFORMATION: CDR3 region of ZR75-1 (IgM) heavy chain

<400> SEQUENCE: 121

Gln Asx Ile Val Ala Phe Ser
1               5

<210> SEQ ID NO 122
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of ZR75-1
      (IgG) heavy chain

<400> SEQUENCE: 122

Ser Gly Phe Asn Phe Asn
1               5

<210> SEQ ID NO 123
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of ZR75-1 (IgG) heavy chain

<400> SEQUENCE: 123

Thr Tyr Ala Met Thr
1               5

<210> SEQ ID NO 124
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of ZR75-1 (IgG) heavy chain

<400> SEQUENCE: 124

Thr Ile Ala Ala Asp Gly Thr Trp Thr Ser Asn Ala Asp Phe Val Arg
1               5                   10                  15

Gly

<210> SEQ ID NO 125
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR3 region of ZR75-1 (IgG) heavy chain

<400> SEQUENCE: 125

Asp Trp Tyr Asp Tyr
1               5
```

```
<210> SEQ ID NO 126
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of SKBR3 (IgG)
      heavy chain

<400> SEQUENCE: 126

Ser Gly Gly Ser Val Ser
1               5

<210> SEQ ID NO 127
<211> LENGTH: 7
<212> TYPE: PRT
<213> ORGANISM: Homo sapiens
<220> FEATURE:
<221> NAME/KEY: DOMAIN
<222> LOCATION: (1)...(7)
<223> OTHER INFORMATION: CDR1 region of SKBR3 (IgG) heavy chain

<400> SEQUENCE: 127

Ser Gly Tyr Tyr Tyr Trp Ser
1               5

<210> SEQ ID NO 128
<211> LENGTH: 16
<212> TYPE: PRT
<213> ORGANISM: Homo sapiens
<220> FEATURE:
<221> NAME/KEY: DOMAIN
<222> LOCATION: (1)...(16)
<223> OTHER INFORMATION: CDR2 region of SKBR3 (IgG) heavy chain

<400> SEQUENCE: 128

Tyr Ile Tyr Tyr Asn Gly Ser Thr Tyr Glu Asn Pro Ser Leu Lys Ser
1               5                   10                  15

<210> SEQ ID NO 129
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: CDR3 region of SKBR3 (IgG) heavy chain

<400> SEQUENCE: 129

Asp Ile Lys His Thr Tyr Gly Pro Asn
1               5

<210> SEQ ID NO 130
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of SKBR3 (IgA)
      heavy chain

<400> SEQUENCE: 130

Ser Gly Leu Ser Phe Ser
1               5

<210> SEQ ID NO 131
<211> LENGTH: 5
<212> TYPE: PRT
```

```
<213> ORGANISM: Homo sapiens
<220> FEATURE:
<221> NAME/KEY: DOMAIN
<222> LOCATION: (1)...(5)
<223> OTHER INFORMATION: CDR1 region of SKBR3 (IgA) heavy chain

<400> SEQUENCE: 131

Ser Ser Gly Met Asn
1               5

<210> SEQ ID NO 132
<211> LENGTH: 19
<212> TYPE: PRT
<213> ORGANISM: Homo sapiens
<220> FEATURE:
<221> NAME/KEY: DOMAIN
<222> LOCATION: (1)...(19)
<223> OTHER INFORMATION: CDR2 region of SKBR3 (IgA) heavy chain

<400> SEQUENCE: 132

Arg Ile Gly Ser Lys Ala Ala Ser Asp Thr Thr Ser Tyr Ala Ala Ser
1               5                   10                  15

Val Arg Gly

<210> SEQ ID NO 133
<211> LENGTH: 12
<212> TYPE: PRT
<213> ORGANISM: Homo sapiens
<220> FEATURE:
<221> NAME/KEY: DOMAIN
<222> LOCATION: (1)...(12)
<223> OTHER INFORMATION: CDR3 region of SKBR3 (IgA) heavy chain

<400> SEQUENCE: 133

Gln Gly Cys Gly Gly Asp Cys His Ile Pro Lys Met
1               5                   10

<210> SEQ ID NO 134
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of MDA-MB-231
      (IgM) heavy chain

<400> SEQUENCE: 134

Ser Gly Phe Thr Phe Ser
1               5

<210> SEQ ID NO 135
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of MDA-MB-231 (IgM) heavy chain

<400> SEQUENCE: 135

Ser Tyr Trp Met Asp
1               5

<210> SEQ ID NO 136
<211> LENGTH: 17
<212> TYPE: PRT
<213> ORGANISM: Homo sapiens
<220> FEATURE:
```

```
<221> NAME/KEY: DOMAIN
<222> LOCATION: (1)...(17)
<223> OTHER INFORMATION: CDR2 region of MDA-MB-231 (IgM) heavy chain

<400> SEQUENCE: 136

Arg Ile Ser Pro Asp Gly Arg Thr Thr Thr Tyr Ala Asp Ser Val Glu
1               5                   10                  15
Gly

<210> SEQ ID NO 137
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: CDR3 region of MDA-MB-231 (IgM) heavy chain

<400> SEQUENCE: 137

Gly Tyr Leu Ser Ser His
1               5

<210> SEQ ID NO 138
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of Lung Cancer
      heavy chain

<400> SEQUENCE: 138

Ser Gly Tyr Thr Phe Gly
1               5

<210> SEQ ID NO 139
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of Lung Cancer heavy chain

<400> SEQUENCE: 139

Thr Tyr Trp Ile Gly
1               5

<210> SEQ ID NO 140
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of Lung Cancer heavy chain

<400> SEQUENCE: 140

Ile Ile Tyr Pro Gly Asp Ser Asp Thr Thr Tyr Ser Pro Ser Phe Arg
1               5                   10                  15
Gly

<210> SEQ ID NO 141
<211> LENGTH: 10
<212> TYPE: PRT
<213> ORGANISM: Homo sapiens
<220> FEATURE:
```

```
<221> NAME/KEY: DOMAIN
<222> LOCATION: (1)...(10)
<223> OTHER INFORMATION: CDR3 region of Lung Cancer heavy chain

<400> SEQUENCE: 141

Trp Asp Val Met Ile Gly Phe Tyr Thr Ala
1               5                   10

<210> SEQ ID NO 142
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of Dakiki
      heavy chain

<400> SEQUENCE: 142

Ser Gly Phe Thr Phe Ser
1               5

<210> SEQ ID NO 143
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of Dakiki heavy chain

<400> SEQUENCE: 143

Asp Tyr Gly Met Thr
1               5

<210> SEQ ID NO 144
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of Dakiki heavy chain

<400> SEQUENCE: 144

Gly Ile Thr Ser Ser Val Leu Thr Thr Tyr Tyr Ala Asp Ser Val Lys
1               5                   10                  15

Gly

<210> SEQ ID NO 145
<211> LENGTH: 9
<212> TYPE: PRT
<213> ORGANISM: Homo sapiens
<220> FEATURE:
<221> NAME/KEY: DOMAIN
<222> LOCATION: (1)...(9)
<223> OTHER INFORMATION: CDR3 region of Dakiki heavy chain

<400> SEQUENCE: 145

Ala Gln Gly Phe Ala Pro Pro Ala Ser
1               5

<210> SEQ ID NO 146
<211> LENGTH: 6
<212> TYPE: PRT
<213> ORGANISM: Homo sapiens
<220> FEATURE:
<221> NAME/KEY: PEPTIDE
<222> LOCATION: (1)...(6)
```

<223> OTHER INFORMATION: Last 6 amino acids in FR1 region of IM-9 heavy
      chain

<400> SEQUENCE: 146

Ser Gly Phe Arg Phe Asp
1               5

<210> SEQ ID NO 147
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of IM-9 heavy chain

<400> SEQUENCE: 147

Asp Tyr Ala Met His
1               5

<210> SEQ ID NO 148
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of IM-9 heavy chain

<400> SEQUENCE: 148

Gly Ile Ser Trp Asn Ser Asp Thr Ile Asp Tyr Ala Asp Ser Val Lys
1               5                   10                  15

Gly

<210> SEQ ID NO 149
<211> LENGTH: 14
<212> TYPE: PRT
<213> ORGANISM: Homo sapiens
<220> FEATURE:
<221> NAME/KEY: DOMAIN
<222> LOCATION: (1)...(14)
<223> OTHER INFORMATION: CDR3 region of IM-9 heavy chain

<400> SEQUENCE: 149

Thr Lys Glu Gly Gly Val Thr Asp Ile Asp Pro Phe Asp Ile
1               5                   10

<210> SEQ ID NO 150
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of MC116 heavy
      chain

<400> SEQUENCE: 150

Ser Gly Tyr Arg Phe Thr
1               5

<210> SEQ ID NO 151
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of MC116 heavy chain

```
<400> SEQUENCE: 151

Gly Tyr Tyr Met His
1               5

<210> SEQ ID NO 152
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of MC116 heavy chain

<400> SEQUENCE: 152

Arg Ile Asn Pro Asn Ser Gly Gly Ile Asn Tyr Ala Gln Arg Phe Gln
1               5                   10                  15

Gly

<210> SEQ ID NO 153
<211> LENGTH: 10
<212> TYPE: PRT
<213> ORGANISM: Homo sapiens
<220> FEATURE:
<221> NAME/KEY: DOMAIN
<222> LOCATION: (1)...(10)
<223> OTHER INFORMATION: CDR3 region of MC116 heavy chain

<400> SEQUENCE: 153

Thr Arg Glu Asp Ser Gly Ser Tyr Glu Tyr
1               5                   10

<210> SEQ ID NO 154
<211> LENGTH: 6
<212> TYPE: PRT
<213> ORGANISM: Homo sapiens
<220> FEATURE:
<221> NAME/KEY: DOMAIN
<222> LOCATION: (1)...(6)
<223> OTHER INFORMATION: Last 6 amino acids in FR1 region of Daudi heavy
      chain

<400> SEQUENCE: 154

Ser Gly Tyr Ser Ile Thr
1               5

<210> SEQ ID NO 155
<211> LENGTH: 5
<212> TYPE: PRT
<213> ORGANISM: Homo sapiens
<220> FEATURE:
<221> NAME/KEY: DOMAIN
<222> LOCATION: (1)...(5)
<223> OTHER INFORMATION: CDR1 region of Daudi heavy chain

<400> SEQUENCE: 155

Ser Tyr Tyr Ile His
1               5

<210> SEQ ID NO 156
<211> LENGTH: 17
<212> TYPE: PRT
<213> ORGANISM: Homo sapiens
<220> FEATURE:
<221> NAME/KEY: DOMAIN
<222> LOCATION: (1)...(17)
<223> OTHER INFORMATION: CDR2 region of Daudi heavy chain

<400> SEQUENCE: 156
```

```
Lys Thr Asp Asn Asp Gly Arg Asp Ala Asp Tyr Ala Gln Arg Phe Gln
1               5                  10                  15

Gly

<210> SEQ ID NO 157
<211> LENGTH: 11
<212> TYPE: PRT
<213> ORGANISM: Homo sapiens
<220> FEATURE:
<221> NAME/KEY: DOMAIN
<222> LOCATION: (1)...(11)
<223> OTHER INFORMATION: CDR3 region of Daudi heavy chain

<400> SEQUENCE: 157

Val Arg Glu Asn Gly Gln Lys Cys Phe Asp Tyr
1               5                  10

<210> SEQ ID NO 158
<211> LENGTH: 57
<212> TYPE: DNA
<213> ORGANISM: Homo sapiens
<220> FEATURE:
<221> NAME/KEY: CDS
<222> LOCATION: (1)...(57)
<220> FEATURE:
<221> NAME/KEY: misc_feature
<222> LOCATION: (1)...(57)
<223> OTHER INFORMATION: H chain variable region signal peptide

<400> SEQUENCE: 158 atg aga tgg agc tgt atc atc ctc ttc ttg gta gca aca gct aca ggt      48
Met Arg Trp Ser Cys Ile Ile Leu Phe Leu Val Ala Thr Ala Thr Gly
1               5                  10                  15 gtc agc tcc                                                          57
Val Ser Ser <210> SEQ ID NO 159
<211> LENGTH: 339
<212> TYPE: DNA
<213> ORGANISM: Homo sapiens
<220> FEATURE:
<221> NAME/KEY: CDS
<222> LOCATION: (1)...(339)
<220> FEATURE:
<221> NAME/KEY: misc_feature
<222> LOCATION: (1)...(339)
<223> OTHER INFORMATION: H chain variable region

<400> SEQUENCE: 159 cag gtc caa ctg cag cag cct ggg gct gag ctt gtg atg cct ggg gct      48
Gln Val Gln Leu Gln Gln Pro Gly Ala Glu Leu Val Met Pro Gly Ala
1               5                  10                  15 tca gtg aag atg tcc tgc aag gct tct ggc tac aca ttc act gac tac      96
Ser Val Lys Met Ser Cys Lys Ala Ser Gly Tyr Thr Phe Thr Asp Tyr
                20                  25                  30 tgg atg cac tgg gtg aag cag agg cct gga caa ggc ctt gag tgg atc     144
Trp Met His Trp Val Lys Gln Arg Pro Gly Gln Gly Leu Glu Trp Ile
            35                  40                  45 gga gcg att gat act tct gat agt tat act agg tac aat caa aag ttc     192
Gly Ala Ile Asp Thr Ser Asp Ser Tyr Thr Arg Tyr Asn Gln Lys Phe
        50                  55                  60 aag gac aag gcc aca ttg act gta gac gaa tcc tcc agc aca gcc ttc     240
Lys Asp Lys Ala Thr Leu Thr Val Asp Glu Ser Ser Ser Thr Ala Phe
65                  70                  75                  80 atg cag ctc agc agc ctg aca tct gag gac tct gcg gtc tat tac tgt     288
Met Gln Leu Ser Ser Leu Thr Ser Glu Asp Ser Ala Val Tyr Tyr Cys
```

|  |  |
|---|---|
| 85 90 95 | |
| gca aga tcc atc tat gac tgg ggc caa ggg act ctg gtc act gtc tct<br>Ala Arg Ser Ile Tyr Asp Trp Gly Gln Gly Thr Leu Val Thr Val Ser<br>100 105 110 | 336 |
| gca<br>Ala | 339 |

<210> SEQ ID NO 160
<211> LENGTH: 63
<212> TYPE: DNA
<213> ORGANISM: Homo sapiens
<220> FEATURE:
<221> NAME/KEY: CDS
<222> LOCATION: (1)...(63)
<220> FEATURE:
<221> NAME/KEY: misc_feature
<222> LOCATION: (1)...(63)
<223> OTHER INFORMATION: L chain variable region - signal peptide

<400> SEQUENCE: 160

|  |  |
|---|---|
| atg gaa tca cag acc cag gtc ctc atg ttt ctt ctg ctc tgg gta tct<br>Met Glu Ser Gln Thr Gln Val Leu Met Phe Leu Leu Leu Trp Val Ser<br>1 5 10 15 | 48 |
| ggt ggt gcc tgt gca<br>Gly Gly Ala Cys Ala<br>20 | 63 |

<210> SEQ ID NO 161
<211> LENGTH: 339
<212> TYPE: DNA
<213> ORGANISM: Homo sapiens
<220> FEATURE:
<221> NAME/KEY: CDS
<222> LOCATION: (1)...(339)
<220> FEATURE:
<221> NAME/KEY: misc_feature
<222> LOCATION: (1)...(339)
<223> OTHER INFORMATION: L chain variable region

<400> SEQUENCE: 161

|  |  |
|---|---|
| gac att gtg atg aca cag tct cca tcc tcc ctg gct atg tca gta gga<br>Asp Ile Val Met Thr Gln Ser Pro Ser Ser Leu Ala Met Ser Val Gly<br>1 5 10 15 | 48 |
| cag aag gtc act atg agc tgc aag tcc agt cag agc ctt tta aat agt<br>Gln Lys Val Thr Met Ser Cys Lys Ser Ser Gln Ser Leu Leu Asn Ser<br>20 25 30 | 96 |
| agc aat caa aag agc tat ttg gcc tgg tac cag cag aaa cca gga cag<br>Ser Asn Gln Lys Ser Tyr Leu Ala Trp Tyr Gln Gln Lys Pro Gly Gln<br>35 40 45 | 144 |
| tct cct aaa ctt ctg gta tac ttt gca tcc act agg gaa tct ggg gtc<br>Ser Pro Lys Leu Leu Val Tyr Phe Ala Ser Thr Arg Glu Ser Gly Val<br>50 55 60 | 192 |
| cct gat cgc ttc ata ggc agt gga tct ggg aca gat ttc act ctt acc<br>Pro Asp Arg Phe Ile Gly Ser Gly Ser Gly Thr Asp Phe Thr Leu Thr<br>65 70 75 80 | 240 |
| atc agc agt gtg cag gct gaa gac ctg gca gat tac ttc tgt cag caa<br>Ile Ser Ser Val Gln Ala Glu Asp Leu Ala Asp Tyr Phe Cys Gln Gln<br>85 90 95 | 288 |
| cat tat agc act ccg tcc acg ttc gga ggg ggg acc aag ctg gaa ata<br>His Tyr Ser Thr Pro Ser Thr Phe Gly Gly Gly Thr Lys Leu Glu Ile<br>100 105 110 | 336 |
| aaa<br>Lys | 339 |

The invention claimed is:

1. A molecule that is immunoreactive with RP215 monoclonal antibody, but not significantly immunoreactive with antihuman IgG, said molecule consisting of an FR1 and CDR1 sequence of CA215 and a carbohydrate, wherein said carbohydrate is coupled to a threonine or serine glycosylation site proximal to the junction between FR1 and CDR1.

2. The molecule of claim 1, which is coupled to a heterologous moiety.

3. A composition comprising the molecule of claim 1.

* * * * *